(12) United States Patent
Kiesel et al.

(10) Patent No.: US 7,358,476 B2
(45) Date of Patent: Apr. 15, 2008

(54) SENSING PHOTONS FROM OBJECTS IN CHANNELS

(75) Inventors: Peter Kiesel, Palo Alto, CA (US); Meng H. Lean, Santa Clara, CA (US); Oliver Schmidt, Palo Alto, CA (US); Armin R. Völkel, Mountain View, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 162 days.

(21) Appl. No.: 11/315,992

(22) Filed: Dec. 22, 2005

(65) Prior Publication Data

US 2007/0145249 A1 Jun. 28, 2007

(51) Int. Cl.
*G01J 3/50* (2006.01)

(52) U.S. Cl. ............... 250/208.2; 250/226; 250/578.1; 356/410; 356/411; 356/434; 356/435

(58) Field of Classification Search ............. 250/208.2, 250/578.1; 365/409–411
See application file for complete search history.

(56) References Cited

U.S. PATENT DOCUMENTS

| | | | |
|---|---|---|---|
| 2,708,389 A | | 5/1955 | Kavanagh |
| 3,973,118 A | | 8/1976 | LaMontagne |
| 4,081,277 A | | 3/1978 | Brault et al. |
| 4,514,257 A | * | 4/1985 | Karlsson et al. ............... 162/49 |
| 4,573,796 A | * | 3/1986 | Martin et al. ............... 356/318 |
| 4,764,670 A | | 8/1988 | Pace et al. |
| 4,957,371 A | | 9/1990 | Pellicori et al. |
| 4,976,542 A | | 12/1990 | Smith |

(Continued)

FOREIGN PATENT DOCUMENTS

WO    WO 95/20144    7/1995

(Continued)

OTHER PUBLICATIONS

Adams, M.L., Enzelberger, M., Quake, S., and Scherer, A., "Microfluidic integration on detector arrays for absorption and fluorescence micro-spectrometers,"Sensors and Actuators A, vol. 104, 2003, pp. 25-31.

(Continued)

*Primary Examiner*—John R. Lee
(74) *Attorney, Agent, or Firm*—Leading-Edge Law Group, PLC; James T. Beran

(57) ABSTRACT

A fluidic structure includes a channel and along the channel is a series of sensing components to obtain information about objects traveling within the channel, such as droplets or other objects carried by fluid. At least one sensing component includes a set of cells of a photosensor array. The set of cells photosense a range of photon energies that emanate from objects, and include a subset of cells that photosense within subranges. A processor can receive information about objects from the sensing components and use it to obtain spectral information. The processor can perform an initial analysis using information from one set of sensing components and, based on the results, control a fluidic device in the channel, such as a gate, to retain objects, such as for concentration and more detailed analysis by other sensing components, or to purge objects from the channel.

32 Claims, 13 Drawing Sheets

U.S. PATENT DOCUMENTS

| | | | |
|---|---|---|---|
| 5,144,498 A | 9/1992 | Vincent | |
| 5,166,755 A | 11/1992 | Gat | |
| 5,305,082 A | 4/1994 | Bret | |
| 5,370,842 A * | 12/1994 | Miyazaki et al. | 422/82.06 |
| 5,572,328 A | 11/1996 | Fouckhardt et al. | |
| 5,682,038 A * | 10/1997 | Hoffman | 250/458.1 |
| 5,777,329 A | 7/1998 | Westphal et al. | |
| 5,784,507 A | 7/1998 | Holm-Kennedy et al. | |
| 5,792,663 A | 8/1998 | Fry et al. | |
| 5,801,831 A | 9/1998 | Sargoytchev | |
| 5,864,641 A | 1/1999 | Murphy et al. | |
| 5,876,674 A * | 3/1999 | Dosoretz et al. | 422/91 |
| 5,880,474 A * | 3/1999 | Norton et al. | 250/458.1 |
| 6,108,463 A | 8/2000 | Herron et al. | |
| 6,137,117 A | 10/2000 | Feldstein et al. | |
| 6,192,168 B1 | 2/2001 | Feldstein et al. | |
| 6,249,346 B1 | 6/2001 | Chen et al. | |
| 6,275,628 B1 | 8/2001 | Jones et al. | |
| 6,295,130 B1 | 9/2001 | Sun et al. | |
| 6,353,475 B1 | 3/2002 | Jensen et al. | |
| 6,399,405 B1 | 6/2002 | Chen et al. | |
| 6,405,073 B1 | 6/2002 | Crowley et al. | |
| 6,459,080 B1 | 10/2002 | Yin et al. | |
| 6,483,959 B1 | 11/2002 | Singh et al. | |
| 6,490,034 B1 | 12/2002 | Woias et al. | |
| 6,505,775 B1 | 1/2003 | Gu et al. | |
| 6,519,037 B2 | 2/2003 | Jung et al. | |
| 6,525,308 B1 | 2/2003 | Schmidt-Hattenberger | |
| 6,558,945 B1 * | 5/2003 | Kao | 435/287.2 |
| 6,577,780 B2 | 6/2003 | Lockhart | |
| 6,580,507 B2 | 6/2003 | Fry et al. | |
| 6,603,548 B2 | 8/2003 | Church et al. | |
| 6,608,679 B1 | 8/2003 | Chen et al. | |
| 6,630,999 B2 | 10/2003 | Shroder | |
| 6,785,002 B2 | 8/2004 | Zarrabian et al. | |
| 6,800,849 B2 | 10/2004 | Staats | |
| 6,870,149 B2 | 3/2005 | Berezin | |
| 6,887,713 B2 | 5/2005 | Nelson et al. | |
| 2002/0155485 A1 * | 10/2002 | Kao | 435/6 |
| 2003/0000835 A1 | 1/2003 | Witt et al. | |
| 2003/0020915 A1 * | 1/2003 | Schueller et al. | 356/436 |
| 2003/0077660 A1 | 4/2003 | Pien et al. | |
| 2003/0235924 A1 | 12/2003 | Adams et al. | |
| 2004/0027462 A1 * | 2/2004 | Hing | 348/222.1 |
| 2004/0031684 A1 | 2/2004 | Witt | |
| 2004/0032584 A1 | 2/2004 | Honda et al. | |
| 2004/0067167 A1 * | 4/2004 | Zhang et al. | 422/82.05 |
| 2004/0132214 A1 | 7/2004 | Lin et al. | |
| 2004/0141884 A1 | 7/2004 | Unno et al. | |
| 2004/0145738 A1 | 7/2004 | Sun et al. | |
| 2004/0175734 A1 | 9/2004 | Stahler et al. | |
| 2004/0223881 A1 | 11/2004 | Cunningham et al. | |
| 2005/0042615 A1 | 2/2005 | Smith et al. | |
| 2005/0068526 A1 | 3/2005 | Avrutsky | |
| 2005/0084203 A1 | 4/2005 | Kane | |
| 2005/0128479 A1 * | 6/2005 | Gilbert et al. | 356/338 |
| 2006/0039009 A1 | 2/2006 | Kiesel et al. | |
| 2006/0046312 A1 | 3/2006 | Kiesel et al. | |
| 2006/0092413 A1 | 5/2006 | Kiesel et al. | |
| 2006/0121555 A1 | 6/2006 | Lean et al. | |
| 2006/0274313 A1 * | 12/2006 | Gilbert et al. | 356/432 |
| 2007/0070347 A1 * | 3/2007 | Scherer et al. | 356/326 |
| 2007/0116609 A1 * | 5/2007 | Baeuerle et al. | 422/100 |
| 2007/0145236 A1 * | 6/2007 | Kiesel et al. | 250/208.1 |
| 2007/0146704 A1 * | 6/2007 | Schmidt et al. | 356/338 |

FOREIGN PATENT DOCUMENTS

| | | |
|---|---|---|
| WO | WO 00/62050 | 10/2000 |

OTHER PUBLICATIONS

Singh, K., Liu, C., Capjack, C., Rosmus, W., and Backhouse, C.J., "Analysis of cellular structure by light scattering measurements in a new cytometer design based on a liquid-core waveguide", IEEE Proc.-Nanobiotechnol., vol. 151, No. 1, Feb. 2004, pp. 10-16.

Agilent Technologies, "Agilent 83453B High-Resolution Spectrometer—Technical Specifications", Feb. 2005, pp. 1-8.

Liu, G.L., and Lee, L.P., "Nanowell surface enhanced Raman scattering arrays fabricated by soft-lithography for label-free biomolecular detections in integrated microfluidics", Applied Physics Letters, vol. 87, 2005, pp. 1-3.

Devasenathipathy, S., and Santiago, J.G., "3 Electrokinetic Flow Diagnostics" in Breuer, K.S., Ed., Micro-and Nano-Scale Diagnostic Techniques, Springer Verlag, New York, 2003, pp. 121-166.

Becker, H., and Gartner, C., "Polymer microfabrication methods for microfluidic analytical applications", Electrophoresis, vol. 21, 2000, pp. 12-26.

Jones, T.B., Gunji, M. Washizu, M., and Feldman, M.J., "Dielectrophoretic liquid actuation and nanodroplet formation", Journal of Applied Physics, vol. 89, No. 2, 2001, pp. 1441-1448.

"Developing technology: HPLC-Chip/MS", Agilent Technologies, printed from www.chem.agilent.com on Aug. 2, 2005, 2 pages.

Singh, K., and Goddard, N.J., "Leaky ARROW Waveguides for Optical Chemical and Biosensors", (Abstract Submitted to Biosensors 1998), printed from dias.umist.ac.uk on Aug. 1, 2005, 2 pages.

"Abstracts of Published Work", printed from dias.umist.ac.uk on Aug. 1, 2005, 3 pages.

Goddard, N.J., Singh, K., Bounaira, F., Holmes, R.J., Baldock, S.J., Pickering, L.W., Fielden, P.R., and Snook, R.D., Anti-Resonant Reflecting Optical.

Waveguides (ARROW), as Optimal Optical Detectors for MicroTAS Applications, printed from dias.umist.ac.uk on Aug. 1, 2005, pp. 1-5.

Sivaprakasam, V., Huston, A., Eversole, J., and Scotto, C., Multiple UV Wavelength Excitation and Fluorescence of Bioaerosols, 2nd Joint Conference on Point Detection, Williamsburg, VA, 2004, 10 pages.

Koch, M., Evans, A.G.R., and Brunnschweiler, A., "Design and fabrication of a micromachined Coulter counter", J. Micromech. Microeng. 9, 1999, pp. 159-161.

"Developing technology: HPLC-Chip/MS", Agilent Technologies, printed from www.chem.agilent.com on Aug. 2, 2005, 2 pages.

Singh, K., and Goddard, N.J., "Leaky ARROW Waveguides for Optical Chemical and Biosensors", (Abstract Submitted to Biosensors 1998), printed from dias.umist.ac.uk on Aug. 1, 2005, 2 pages.

"Abstracts of Published Work", printed from dias,umist.ac.uk on Aug. 1, 2005, 3 pages.

Goddard, N.J., Singh, K., Bounaira, F., Holmes, R.J., Baldock, S.J., Pickering, L.W., Fielden, P.R., and Snook, R.D., Anti-Resonant Reflecting Optical.

Sivaprakasam, V., Huston, A., Eversole, J., and Scotto, C., Multiple UV Wavelength Excitation and Flurescence of Bioaerosols, 2nd Joint Conference on Point Detection, Williamsburg, VA, 2004, 10 pages.

Koch, M., Evans, A.G.R., and Brunnschweiler, A., "Design and fabrication of a micromachines Coulter counter", J. Micromech. Microeng. 9, 1999, pp. 159-161.

* cited by examiner

FIG. 6
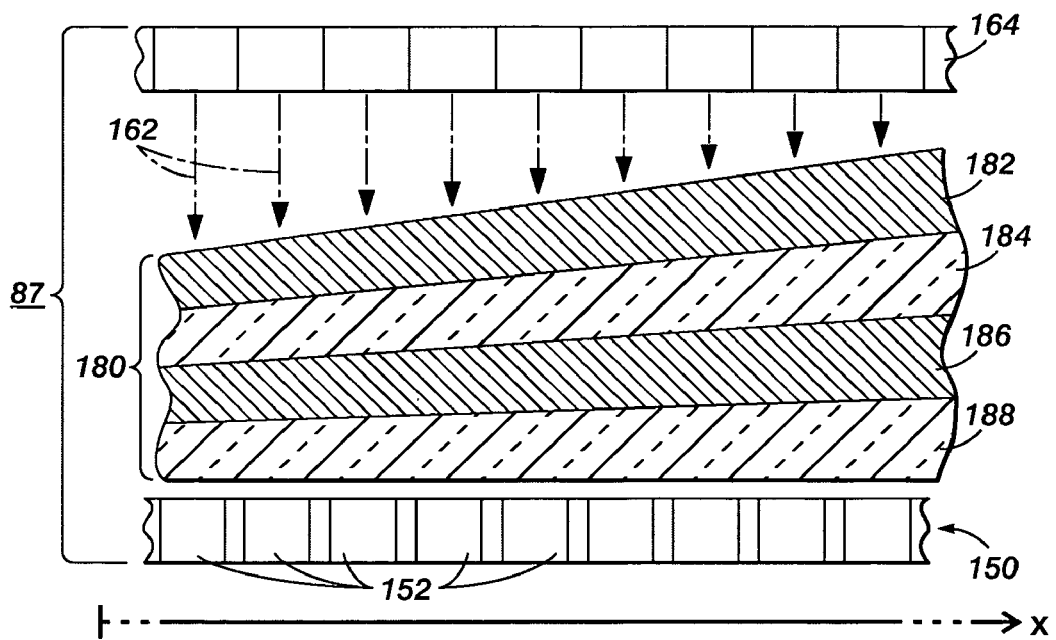
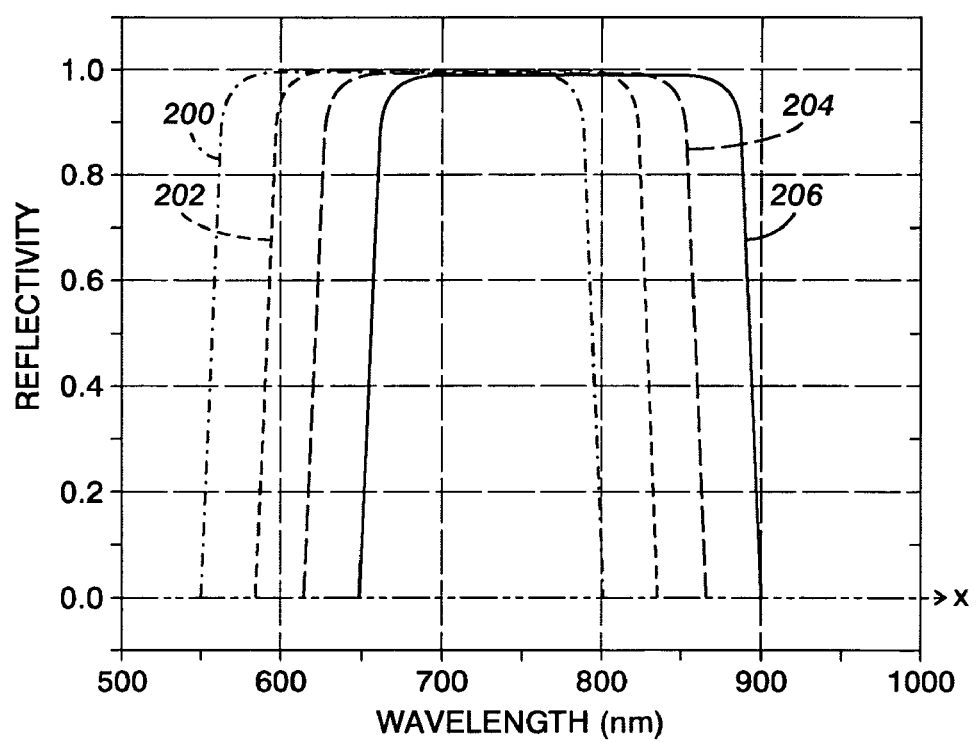
FIG. 7

FIG. 12
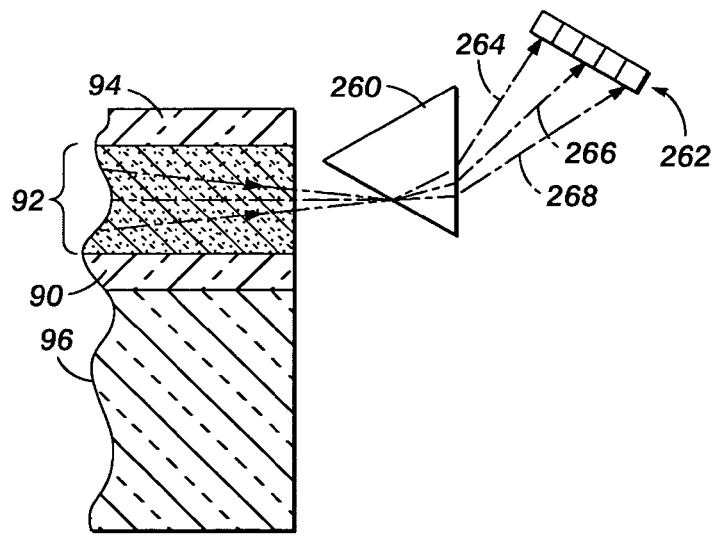
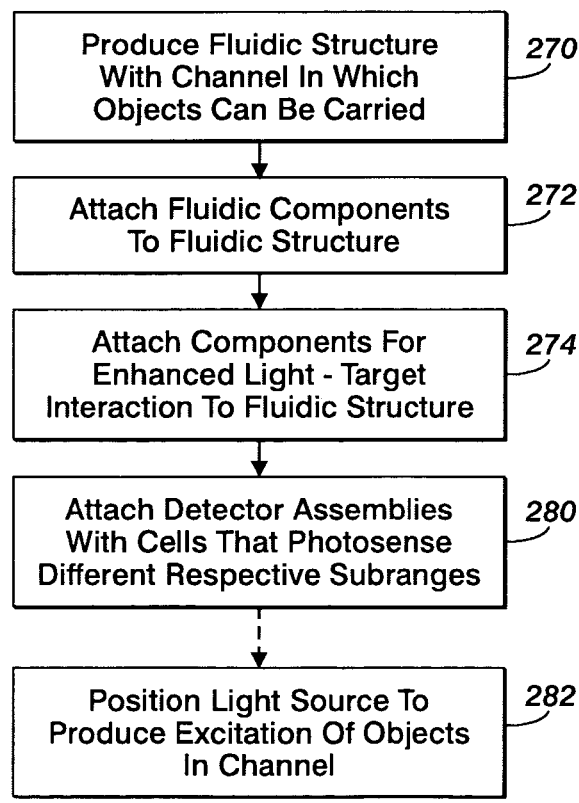
FIG. 13

FIG. 14
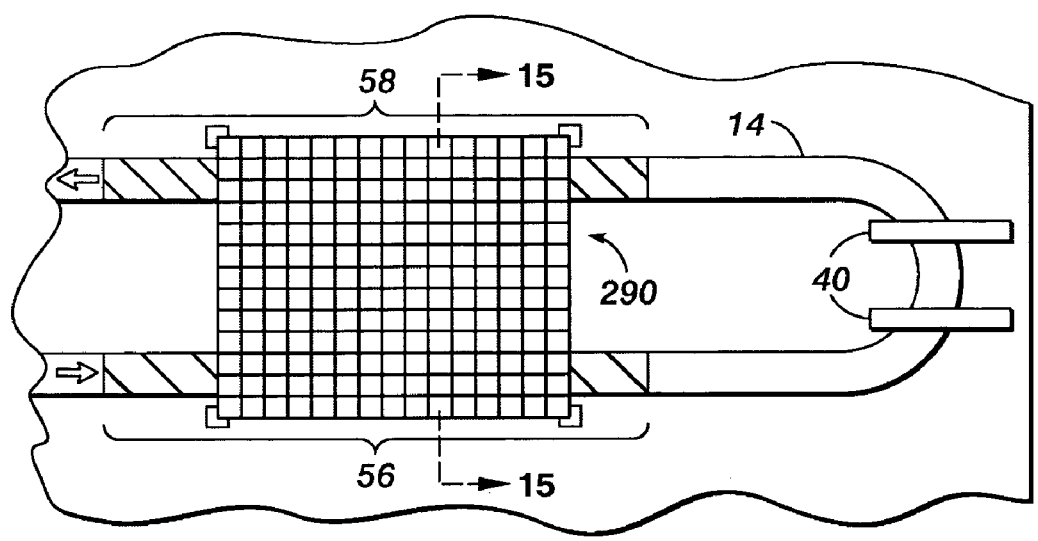
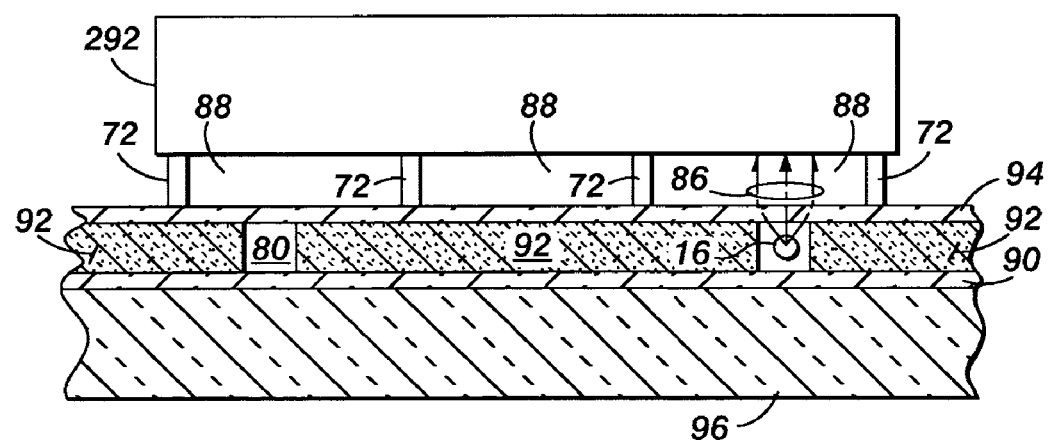
FIG. 15

FIG. 16
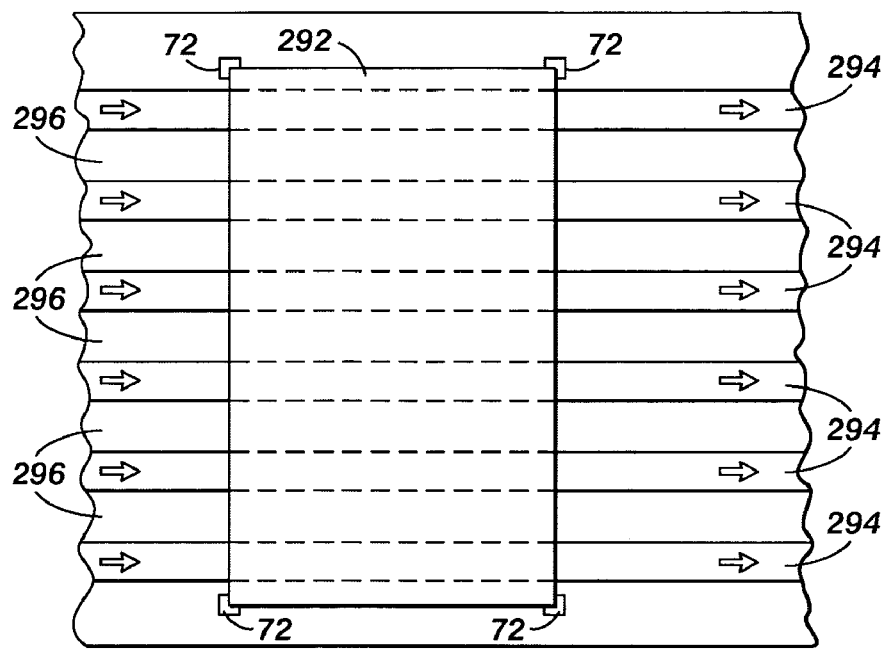
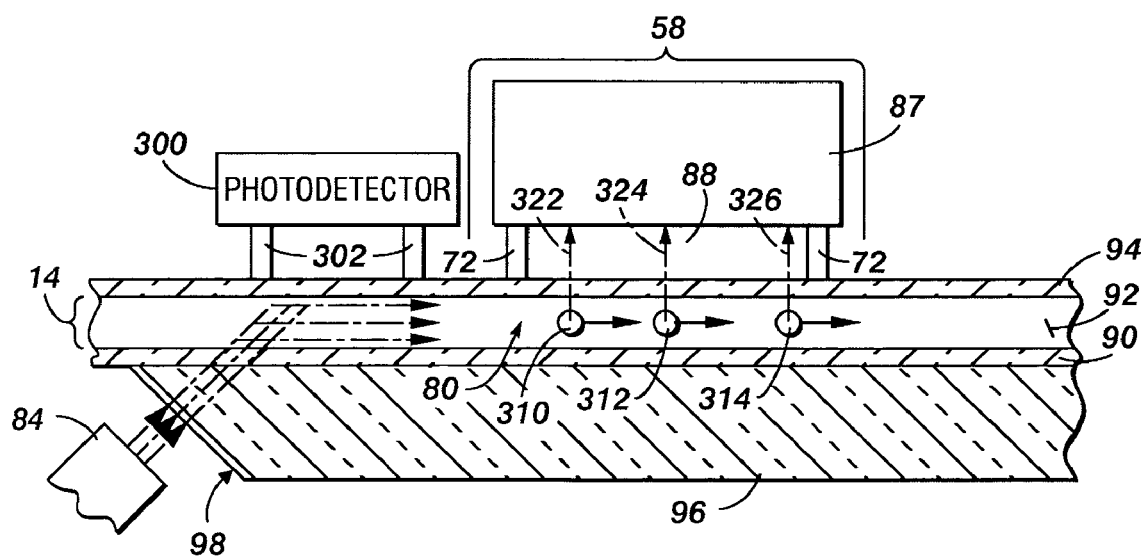
FIG. 17

FIG. 19
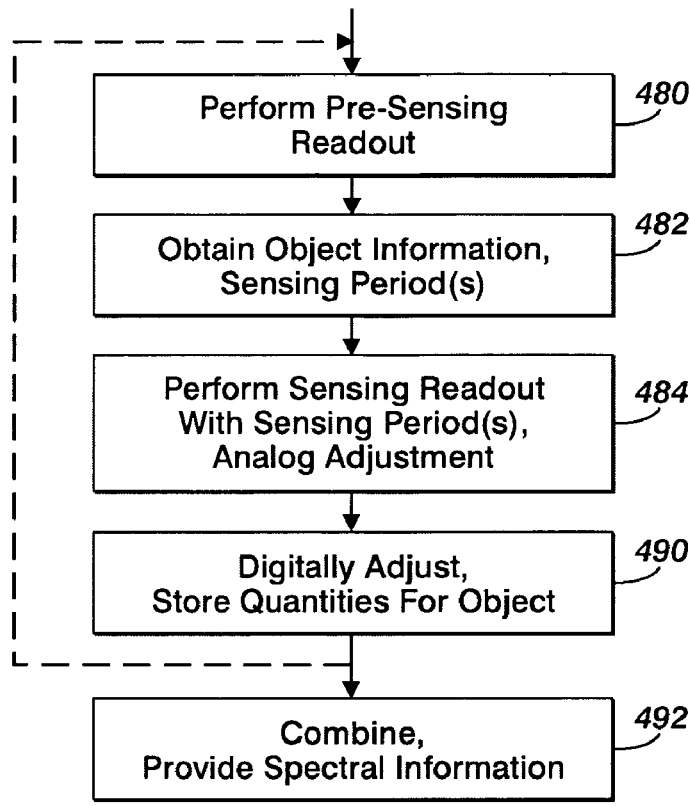
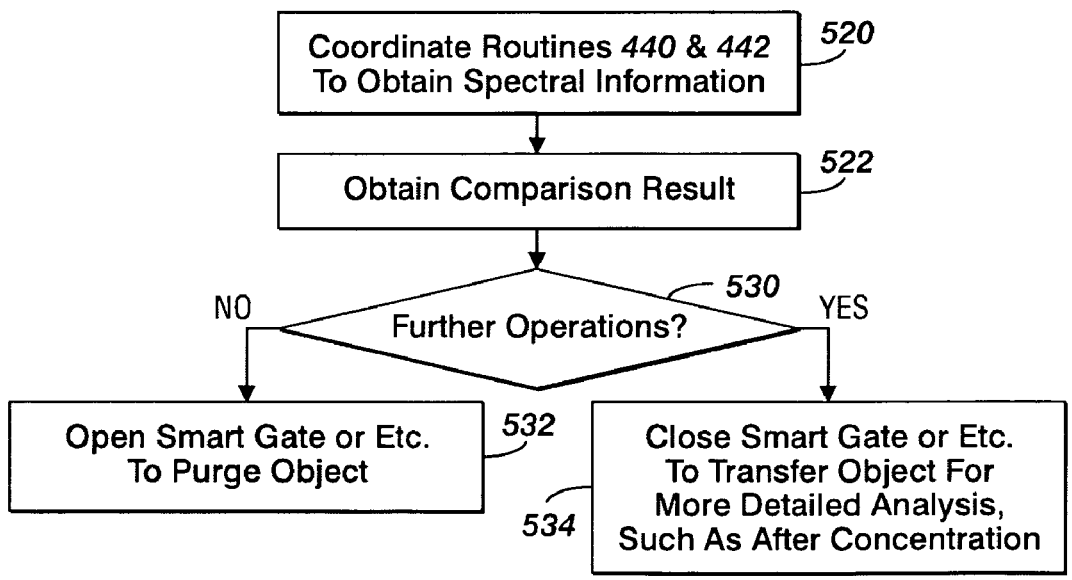
FIG. 20

SENSING PHOTONS FROM OBJECTS IN CHANNELS

The present application is related to the following co-pending applications, each of which is hereby incorporated by reference in its entirety: "Chip-Size Wavelength Detector", U.S. patent application Ser. No. 10/922,870; "Biosensor Using Microdisk Laser", U.S. patent application Ser. No. 10/930,758; "Anti-resonant Waveguide Sensors", U.S. patent application Ser. No. 10/976,434; "Bio-Enrichment Device to Enhance Sample Collection and Detection", U.S. patent application Ser. No. 11/007,121; "Photosensing Throughout Energy Range and in Subranges", U.S. patent application Ser. No. 11/316,438 "Sensing Photon Energies of Optical Signals", U.S. patent application Ser. No. 11/315,926; "Providing Light To Channels Or Portions", U.S. patent application Ser. No. 11/316,660 "Sensing Photon Energies Emanating from Channels or Moving Objects", U.S. patent application Ser. No. 11/315,386; "Transmitting Light With Photon Energy Information", U.S. patent application Ser. No. 11/316,241 "Obtaining Analyte Information", U.S. patent application Ser. No. 11/316,303; and "Propagating Light to be Sensed", U.S. patent application Ser. No. 11/315,387.

BACKGROUND OF THE INVENTION

The present invention relates generally to photosensing, and more particularly to sensing photons emanating from objects in channels.

U.S. Pat. No. 5,166,755 describes a spectrometer apparatus in which a spectrum resolving sensor contains an opto-electronic monolithic array of photosensitive elements and a continuous variable optical filter. The filter can include a variable thickness coating formed into a wedge shape on a substrate or directly on the surface of the array. If polychromatic light, such as light reflected from a sample or a strip of a scene viewed from a spacecraft, passes through the variable filter and is spectrally resolved before incidence on the array, the output of all the elements in the array provides the spectral contents of the polychromatic light.

U.S. Pat. No. 6,580,507 describes a multiple-longitudinal flow cell channel system in which an array detector is positioned to monitor radiation from at least two of multiple flow cell channels, at separate groupings of pixels on the detector. Absorption or fluorescence of analytes in response to electromagnetic radiation can be monitored, where the analytes are contained in fluid flowing through the channels. Commonly available detector chips suitable for detecting visible wavelengths can be thinly coated with a lumagen or other fluorophore to facilitate UV sensitivity and mediate consistency of wavelength input to detector pixels.

It would be advantageous to have improved techniques for sensing photons emanating from objects in channels.

SUMMARY OF THE INVENTION

The invention provides various exemplary embodiments, including methods, apparatus, and systems. In general, the embodiments are implemented with fluidic structures with channels and sensing components along the channels.

These and other features and advantages of exemplary embodiments of the invention are described below with reference to the accompanying drawings.

BRIEF DESCRIPTION OF THE DRAWINGS

FIG. 6 is a schematic cross-sectional view of another implementation of an assembly that can be used in FIG. 2.

FIG. 7 is a graph illustrating the laterally varying light transmission properties of a transmission structure in FIG. 6.

FIG. 12 is a schematic diagram showing use of a prism in an alternative implementation to those of FIGS. 10 and 11.

FIG. 13 is a flowchart showing general operations that can be performed in producing an analyzer as in FIG. 1.

FIG. 14 is a schematic drawing of an alternative implementation of part of an analyzer on a fluidic structure as in FIG. 1.

FIG. 15 is a schematic cross-sectional view of the alternative implementation in FIG. 14, taken along the line 15-15.

FIG. 16 is a schematic plan view of a portion of an alternative implementation of an analyzer as in FIG. 1.

FIG. 17 is a schematic cross-sectional view of an alternative implementation of the sensing component in FIG. 2.

FIG. 19 is a flowchart showing general operations implementing a detect, readout, and combine routine as in FIG. 18.

FIG. 20 is a flowchart showing general operations implementing an object selection routine as in FIG. 18.

DETAILED DESCRIPTION

Figure 1:
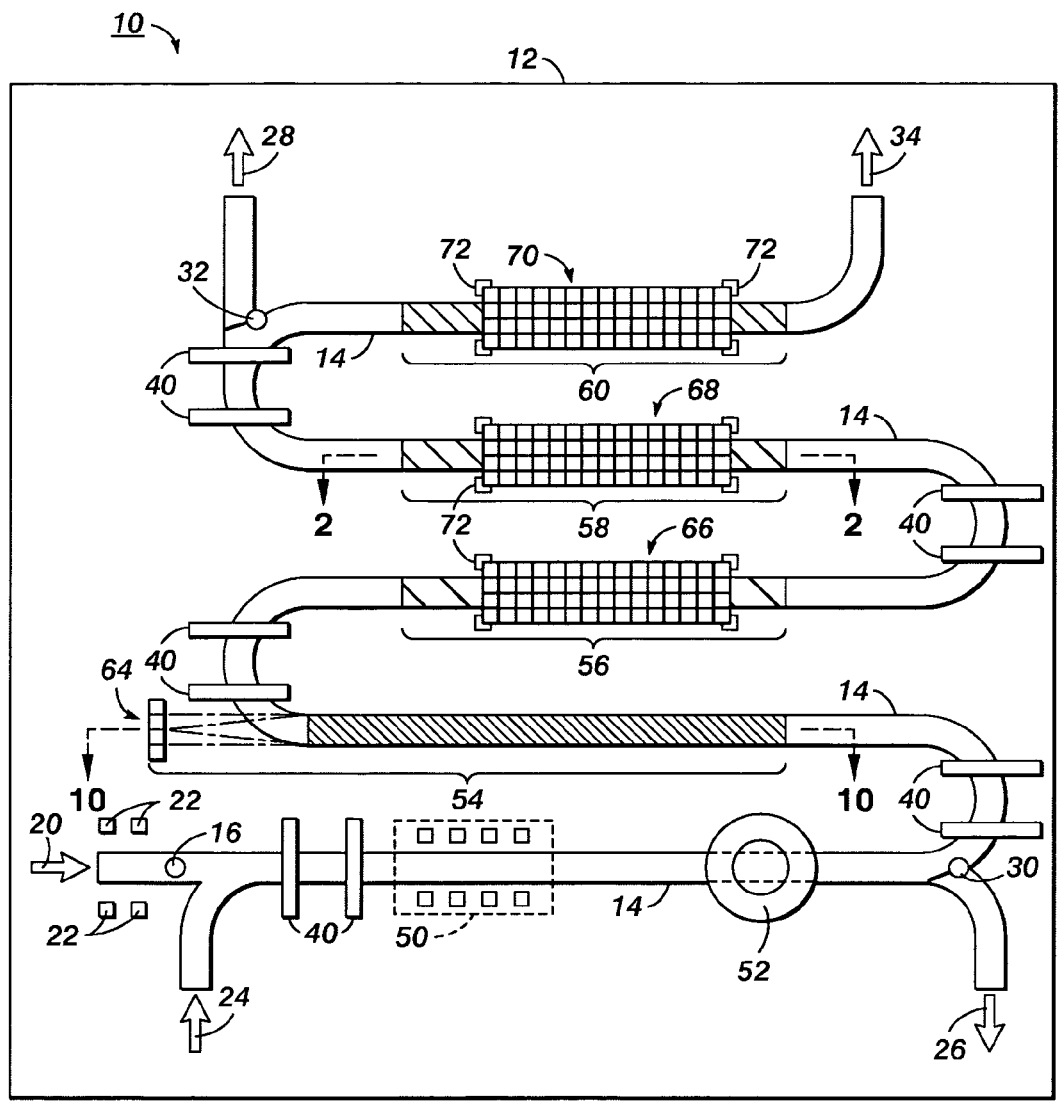
FIG. 1 is a schematic diagram of an analyzer on a fluidic structure.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. The term "photon" refers herein to a quantum of light, and the term "photon energy" refers herein to the energy of a photon.

The various exemplary implementations described below address problems that arise in obtaining information about nanoparticles, microorganisms, bioagents, toxins, and other analytes, such as in aerosols, water, blood, food, and other specimens. One of those problems is the difficulty of obtaining complete spectral information about an analyte rapidly, without specially skilled personnel, and without bulky, expensive equipment as is conventionally used. The difficulty of obtaining complete spectral information is especially problematic for optical characterization of moving fluid-borne analytes that are hard to capture (or where it is not desired to capture them) so that it is necessary to obtain spectral information while they are moving.

Other problems arise due to currently available optical characterization techniques. Optical techniques offer very high sensitivity, but discrimination remains difficult in all wavelength ranges. In addition, optical techniques for identifying analytes are constrained by weak interaction with excitation light and by the need to move a sample from one device to another if more than one detection technique is necessary for unique identification. A further complication is that bioagents dispersed either in an aerosol or in water are typically in such low concentrations that they are below the limit of detection of even the most sensitive available detection techniques; detection of low concentrations is important, because, for example, the ingestion of a single bacterium might lead to fatal consequences.

Some have proposed orthogonal approaches that analyze combined data from a range of different optical detection techniques. Identifying particular species of bioagents is problematic but encouraging results have been obtained with current techniques. It has been shown that two-wavelength fluorescence excitation can provide good class differentiation for individual biomolecules. Class identification in the case of mixtures or in the presence of different environments still appears problematic.

Detection techniques that use polymerase chain reaction (PCR) or specific binding of target molecules to analytes require expensive chemicals and can only be used with analytes for which target molecules are available. Such techniques are also prone to unpredicted results in messy samples contaminated with organic and inorganic dirt. Specific binding is often monitored by optical recognition techniques, such as fluorescence excitation, but this requires the analyte to be tagged with fluorophores and photobleaching restricts the time frame for optical probing. Other methods that do not require labeling measure small refractive index changes causing by specific binding to a probe surface; even where all conditions are right, a specifically bound monolayer is typically very thin (less than 1 nm up to a few nm) and the refractive index change is very small, leading to low signal-to-noise ratios and resulting errors.

Detection techniques that use optical biosensors, especially sophisticated versions based on Raman scattering, IR spectroscopy, or multi-wavelength fluorescence excitation, require bulky optical instruments. Currently available spectrometers are large and expensive systems that split an incident wavelength spectrum into its components with gratings or prisms in order to determine intensity of various wavelength fractions. Expensive and sophisticated mechanical assemblies and complicated software routines are necessary for detection of small wavelength shifts. It is difficult to combine several such detection techniques into a single analysis tool due to size, cost, and the need to move analytes from system to system.

The term "sensing" is used herein in the most generic sense of obtaining information from a physical stimulus; sensing therefore includes actions such as detecting, measuring, and so forth. A "sensing component" is any component that performs sensing.

To "photosense" is to sense photons, and to "photosense quantity" of photons is to obtain information indicating a quantity of the photons. Photons that are photosensed are sometimes referred to herein as "incident photons".

A "photosensor" is used herein to refer generally to any element or combination of elements that senses photons, whether by photosensing quantity or any other information about the photons. A photosensor could, for example, provide an electrical signal or other signal that indicates sensed information, such as a signal indicating quantity of incident photons. If electrical sensing events occur in a photosensor in response to incident photons, the photosensor may integrate or otherwise accumulate the results of the electrical sensing events during a time period referred to herein as a "sensing period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A "fluorescence subrange", for example, is a subrange in which fluorescence emissions occur; an "absorption subrange" is a subrange in which light absorption occurs; and a "scattering subrange" is a subrange in which light scattering occurs.

In general, each application of photosensing has a characteristic energy range, referred to as the "application's energy range", which is the range of photon energies over which it is necessary to obtain information in order that the application satisfies the relevant performance criteria. For example, if an application uses helium arc lamps, its energy range could encompass helium's major emission peaks.

In general, the upper and lower boundaries and widths of ranges and subranges are approximate. To photosense quantity of photons "throughout", "within", or "in" a range or subrange means to obtain information about quantity of photons that are predominantly within the range or subrange. In typical cases, between 60-90% of the sensed quantity of photons having energies within the range or subrange, but the percentage could be lower or higher. In some applications, 90% or even 95% or more of the sensed quantity of photons have energies within the range or subrange. Where an application requires that a minimum percentage or other proportion of sensed quantity of photons have energies within a range or subrange, the minimum percentage or other proportion is referred to herein as the "application's minimum photon proportion".

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations described herein include features characterized as "cells" and "arrays", terms that are used with related meanings: An "array" is an arrangement of "cells". An array on an IC or other support structure may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

A "photosensor array" is an array in which some or all of the cells are or include photosensors. Accordingly, an IC "includes" a photosensor array if the IC includes an array of cells, and at least some of the cells include respective photosensors. A cell that includes a photosensor may also include "cell circuitry", such as circuitry that makes connections with the photosensor, that transfers signals to or from the photosensor, or that performs any other function other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application that includes a photosensor array, circuitry that "responds to" the photosensor array can be any circuitry that, in operation, receives information from the photosensor array about its photosensing results through an electrical connection. Circuitry that responds to a photosensor array could be circuitry in the photosensor array, or it could be peripheral circuitry or other external circuitry, or it could include any suitable combination of array circuitry, peripheral circuitry, and other external circuitry.

FIG. 1 shows schematically some components of analyzer 10 on support structure 12, a fluidic structure. Defined in support structure 12 is serpentine channel 14 through which an object 16 can travel, carried by a fluid or other appropriate substance. Object 16 can, for example, be a droplet or small volume of fluid that includes an analyte to be analyzed.

The term "object" is used herein in the general sense of any distinguishable thing from which light can emanate, whether through emission (e.g. radiation, fluorescence, incandescence, luminescence, etc.), scattering (e.g. reflection, deflection, diffraction, refraction, etc.), or transmission. The light "emanates from" or is simply "from" the object.

Examples of objects that could occur in implementations as described below include droplets, small volumes of fluid, single molecules, agglomerated molecules, molecule clusters, cells, viruses, bacteria, proteins, DNA, microparticles, nanoparticles, and emulsions. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be an "scattering component" of a droplet. An analyte (i.e. a chemical species being investigated) in a droplet can act as a fluorescent, absorbent, or scattering component.

An object "travels" or is caused "to travel" if the object moves through a succession of positions. For example, the object could be conveyed in a fluid, such as a liquid, gas, or aerosol, in which case the object may be referred to as being "carried" by the fluid.

Some exemplary implementations of the invention involve fluidic techniques for causing objects to travel; as noted above, the term "fluid" is used herein to encompass liquids, gasses, and aerosols. The terms "fluidic structure" and "channel" are used herein with related meanings: A "fluidic structure" is a structure that depends for its operation on fluid positioning or fluid flow, such as, for liquids or gases, in response to pressure or, for liquids, as a result of surface tension effects; a "channel" is any tube or other enclosed passage within a fluidic structure through which fluid flows during operation.

An object "travels" within a channel or a portion of a channel or is caused "to travel" within a channel or a portion if the object moves through a succession of positions in the channel or portion. "One object at a time" is caused to travel through a portion of a channel if, from the relevant objects, only one is in the portion at a time. A "fluid propelling component" is a component that pumps or otherwise propels fluid within a channel.

Object 16 enters channel 14 carried by a primary fluid illustrated by arrow 20, and can enter from a supply reservoir (not shown) and a sample well (not shown), with its entry into the primary fluid controlled by metering electrodes 22. The supply reservoir could, for example, be a microfabricated bio-enrichment device with a cell on which concentration occurs, as described in co-pending U.S. patent application Ser. No. 11/007,121, entitled "Bio-Enrichment Device to Enhance Sample Collection and Detection" and incorporated herein by reference in its entirety. Separated bands in the bio-enrichment sample well could be selectively directed into channel 14. Rather than electrical metering, as with electrodes 22, pressure metering could be used. Other possible techniques that could be implemented to provide a droplet or other small object to channel 14 could employ capillary forces or electro-osmotic flow pumps.

Although FIG. 1 illustratively shows an implementation with only one channel 14 receiving analyte samples from a single sample well (not shown) or other analyzer container, analyte 10 could be implemented with any appropriate number of channels similar to channel 14, and with each channel receiving analyte samples from a respective sample well. Furthermore, each of the channels could have a different combination of components suitable to a specific type of analysis such as fluorescence spectroscopy, laser-induced fluorescence spectroscopy (LIF), absorption spectroscopy, excitation spectroscopy, Raman scattering, surface-enhanced Raman scattering (SERS), far-infrared spectroscopy, etc. Each sample well could continuously collect a specific analyte for stationary or post-detection schemes. The channels could be formed by subdividing a broad channel into several parallel channels.

Additional fluid to carry object 16 may enter as shown by arrow 24, such as to permit a constant flow rate or consistent flow independent of the analyte supply. The path followed by the fluid in channel 14 can be controlled through a number of devices. For example, the fluid, together with object 16 if appropriately positioned, can be purged at two outlets as illustrated by arrows 26 and 28 through toggling of valves 30 and 32, respectively, each of which is at a bifurcation junction. Rather than valves, other types of gates could be used, such as electric fields to selectively deflect objects; charged particles could be deflected by Coulomb force, and polarizable particles could be deflected by dielectrophoretic force. If the fluid is not purged by operating valves 30 and 32 or other similar valves (not shown) or by some other type of gate, it is purged at a final outlet from channel 14, illustrated by arrow 34.

The flow of the fluid can be maintained by conventional propulsion components such as electro-osmotic pumps 40 or some suitable hydraulic pressure pump appropriately positioned along the length of channel 14. A wide variety of other propulsion components could be used, including, for example, gas pressure pumps, positive displacement pumps, micro-peristaltic pumps, electro-kinetic pumps, piezo pumps, and thermal mode pumps. Various techniques for fluid propulsion are described in Devasenathipathy, S., and Santiago, J. G., "Electrokinetic Flow Diagnostics", in Breuer, K. S., Ed., *Micro and Nano-Scale Diagnostic Techniques*, Springer-Verlag, New York, 2003, pp. 113-154, incorporated herein by reference. In addition to maintaining flow of fluid, propulsion components can also perform system flush and initial fluid loading functions, with pressure driven techniques. Appropriate circuitry (not shown) can coordinate the various pumps and other components to work in a synchronized manner.

Pressure driven flow creates a parabolic velocity profile due to fluid resistance at the walls of a channel, which leads to band spreading. Spreading and other forms of band distortion will also be evident in fluid passing through one of the serpentine curves in channel 14. Appropriate techniques can be used to track discrete analytes and provide flow cross-section commensurate with analyte size.

Electro-osmotic flow (EOF) results from motion of ions inside the Debye layer due to an applied electric field in a channel direction. A Debye layer forms if the channel walls charge up when in contact with the solvent, e.g. water. The charged wall surface attracts oppositely charged counter ions, which concentrate in a thin layer next to the surface. The Debye layer has a thickness of $$\lambda_D = \left(\frac{\varepsilon kT}{q^2 n}\right)^{1/2},$$

where $\varepsilon$ indicates the dielectric constant, k indicates the Boltzman constant, T indicates the temperature, q indicates the ion charge, and n indicates the concentration of ions. Application of a potential difference in the direction of the channel causes the Debye layer to move with the electric field and, due to viscous drag, to create bulk fluid flow. The velocity profile is flat so that band distortion is a minimum. It should be noted, however, that EOF is dependent on wall charge, which is in turn affected by pH.

Various techniques can be used to control the flow of analytes, such as by directing them into different channels depending on their properties. This allows purging of benign or uninteresting particles, or the use of different detection schemes for different classes of particles that have been identified in initial detection steps. For example, the propulsion components can be coordinated with appropriate additional components for gating, metering, sorting, bifurcating, and otherwise logically controlling flow, such as with valves 30 and 32 and other appropriate devices controlled by switching electrodes and charge control.

Along channel 14 is a series of sensing components, each of which obtains information about object 16 as it travels within a respective straight portion of channel 14; the straight portions are separated by 180-degree curved portions, allowing a compact arrangement of several sensing components and interactive detection. Coulter counter 50 and Mie scatter sensor 52, for example, are conventional sensing components, illustratively along parts of one straight portion of channel 14. Coulter counter 50 is an example of an electrically based particle size detector, and could be implemented as described, for example, in Koch, M., Evans, A. G. R., and Brunnschweiler, A., "Design and Fabrication of a Micromachined Coulter Counter", *J. Micromech. Microeng.*, Vol. 9, 1999, pp. 159-161, incorporated herein by reference. Mie scatter sensor 52 is an example of an optical detector that relies on particle-induced scattering of light entering from the side of channel 14.

Coulter counter 50 can be implemented to size particles in the 1-10 μm range within a continuous liquid stream. The Coulter counter technique should also work for other particle sizes as long as the inner diameter of channel 14 in the sensing region is not more than an order of magnitude larger than the particles being measured. Also, larger particles are harder to handle in microfluidic systems, i.e. fluidic systems in which channels have maximum transverse inner dimensions less than 0.1 mm; in such systems, larger particles tend to sediment if their density is greater than that of the solvent.

In Coulter counter 50, particles suspended in an electrically conducting solution can be drawn through a small aperture between two electrodes. A voltage applied across the aperture creates a sensing zone, and each particle passing through the sensing zone displaces its own volume of conducting liquid. The particle has infinite resistance, even if itself conductive, because polarization effects at the particle-electrolyte interface prevent any current from flowing through the particle itself. Therefore, the particle's resistance causes a momentary increase of impedance across the aperture. This change in impedance produces a tiny current flow that can be received by an amplifier and converted into a voltage pulse large enough for accurate measurement.

The Coulter principle states that the amplitude of this pulse is directly proportional to the volume of the particle, so that scaling pulse heights in volume units provides information about particle size. A size distribution can be obtained and displayed.

Mie scattering is another conventional technique for determining particle size in a free stream. Mie scattering refers to the elastic interaction of electromagnetic waves with particles having diameter at least one-tenth of the wavelength of incident light. The radiation pattern is predominantly forward scatter, with an invariant scattered angular pattern that is symmetrical along the axis of incident light for a perfect sphere. The scattered intensity increases with sphere radius, so that large particles may be distinguished from small particles by the strength of light reflected from their surfaces at a given angle. Mie scattering using light of different wavelengths has been successfully applied to size measurements of single bioaerosol particles.

The series of sensing components also includes optical (e.g. visible or infrared) absorption sensing component 54, first fluorescence sensing component 56, second fluorescence sensing component 58, and Raman scatter sensing component 60. These are merely exemplary, however, and analyzer 10 could include any other suitable combination of sensing components, including some that are not connected in series. In particular, additional sensing components (not shown) could include conventional optical or electrical trigger elements that provide a signal indicating when an analyte with properties meeting certain criteria moves past a position along channel 14. Furthermore, it may be possible to include sensing components for electrical impedance spectroscopy (EIS) for electronic pathology rather than sensing differential resistance for bioparticle sizing.

A signal indicates "spectral information" about photons if it indicates information about quantities of the photons with energies in each of a set of subranges of a range of photon energies. The spectral information could, for example, be a "spectral distribution" in which quantities in non-overlapping subranges are indicated. More specifically, a "complete spectral distribution" is a spectral distribution in which the subranges cover substantially all of an application's energy range. The term "spectral profile" is used herein to refer to a partial or complete spectral distribution for a specific analyte, and could, for example, be one of a number of known spectral profiles collected in a database, referred to herein as a "library of spectral profiles".

A series of sensing components as in FIG. 1 makes it possible to obtain spectral information about moving particles or other objects in order to achieve orthogonal characterization and reliable identification. Characterization is orthogonal if sensing components obtain information about orthogonal characteristics of a moving object, such as by photosensing different ranges of photon energies; sensing components could also be suitable for different intensity ranges. By choosing suitable materials, it is possible to obtain spectral information for the entire range from the deep ultraviolet to the far infrared or even for frequencies in the THz range.

Analyzer 10 can be designed to perform multi-signal analysis for a specific application, whether high wavelength resolution or broadband detection is desired. The technique illustrated in FIG. 1 also takes advantage of the motion of object 16 with a geometry that enables long integration times without sacrificing throughput capacity. Highly sensitive optical characterization methods can be used, such as fluorescence spectroscopy (illustratively in more than one range of photon energies) and Raman spectroscopy. Sivaprakasam, V., Houston, A., Scotto, C., and Eversole, J., "Multiple UV Wavelength Excitation and Fluorescence of Bioaerosols", *Optics* Express, Vol. 12, No. 9 (2004), pp. 4457-4466, have shown that using different UV excitation ranges provides more specific information about an analyte. Also, the use of multi-signal analysis makes it possible to perform reagentless bioagent identification.

Each of sensing components 54, 56, 58, and 60 includes a respective one of ICs 64, 66, 68, and 70, features of which are described in greater detail below. In general, however, each of these ICs includes a photosensor array, and the sensing component includes a set of cells of the photosensor array. The set of cells photosenses photons within a range of photon energies; for example, the sets of cells in ICs 66 and 68 could photosense different ranges of photon energies in the visible to ultraviolet range, and, as noted above, the set of cells in IC 70 could photosense in the infrared. Furthermore, more than one IC, such as ICs 66 and 68, could photosense fluorescing photons that are in the same energy range, but that result from excitation at different wavelengths such as from different LED or laser light sources. As explained in greater detail below, the set of cells for each of sensing components 54, 56, 58 and 60 includes a subset of cells, each of which photosenses in a respective subrange, and the subranges of at least two of the cells are different from each other.

Subranges of photosensing are "different from each other" in a given application if, at the application's minimum photon proportion, the subranges produce distinguishable photosensing results when the application requires. For example, if two subranges are so similar that their photosensing results cannot be distinguished when required, they are not different from each other. It should be noted, however, that subranges that are different from each other can nonetheless overlap or one of them can include another.

As described in greater detail below, sensing components 56, 58, and 60 can each be implemented with any suitable excitation or illumination technique to cause emanation of light from objects. One such technique, for example, is enhanced light-target interaction, which can be accomplished by anti-resonant waveguide techniques or other suitable excitation techniques. An "excitation component" is a component that provides excitation to objects so that photons are emitted from the objects; the excitation could, for example, be electromagnetic wave excitation or a reagent. An "illumination component" is a component that provides light to objects, such as to cause scattering of photons from the objects.

Enhanced light-target interaction is especially important if analyzer 10 is characterizing single particles or low concentrations of biological or chemical agents. In general, an anti-resonant waveguide has a core region surrounded by a cladding layer with a higher refractive index than the core region. Where the core region is a fluid that contains an analyte, light can be guided within the fluid, permitting photonic interaction over an extended length of a channel such as channel 14. As illustrated in FIG. 1, ICs 66, 68, and 70 are therefore supported on spacers 72, providing a suitable gap between each IC and the respective portion of channel 14 to avoid interference with anti-resonant waveguiding.

Anti-resonant waveguide techniques are described in greater detail in co-pending U.S. patent application Ser. No.

10/976,434, entitled "Anti-resonant Waveguide Sensors" and incorporated herein by reference in its entirety. Additional techniques are described in Goddard, N. J., Singh, K., Bounaira, F., Holmes, R. J., Baldock, S. J., Pickering, L. W., Fielden, P. R., and Snook, R. D., "Anti-Resonant Reflecting Optical Waveguides (ARROWs) as Optimal Optical Detectors for MicroTAS Applications", dias.umist.ac.uk/NJG/Abstracts/MicroTAS/MicroTas2.htm, pp. 1-5, and Singh, K., and Goddard, N. J., "Leaky Arrow Waveguides for Optical Chemical and Biosensors", (Abstract Submitted to Biosensors 1998), dias.umist.ac.uk/NJG/Abstracts/Biosensors/ARROW-Biosensors.htm, pp. 1-2, both of which are incorporated herein by reference.

In optical biosensors, the interaction between light and target molecules is typically very weak. Techniques in which light propagates in a longitudinal direction, such as anti-resonant waveguide techniques, can improve the interaction because of the extended length in which interaction occurs. Also, such techniques are very suitable for multi-signal analysis because they are relatively unaffected by changes in wavelength or film thickness. More particularly, in contrast to excitation techniques that use evanescent fields of ordinary waveguides and therefore require very small channels, fluidic channels with maximum transverse dimensions as great as a few millimeters can be used as anti-resonant waveguides. Suitable configurations can include, for example, an aerosol in a glass capillary tube or a liquid film between glass slides. The excitation could be with visible light, ultraviolet light, infrared light, radiation in the terahertz range, or any other appropriate electromagnetic radiation. Examples of specific sensing components employing anti-resonant waveguide techniques are described in greater detail below.

The use of anti-resonant waveguides and other techniques for enhanced light-target interaction may require additional mechanisms to suppress background excitation light. The use of an anti-resonant waveguide, by itself, strongly reduces background detected by a photosensor array located parallel to the waveguide, as illustrated below. In addition, if each cell of a photosensor array is only photosensing a subrange of photon energies, additional background suppression occurs because other photon energies will not be photosensed; in some implementations, for example, they may be reflected from a coating over the photosensor array. Additional background suppression can be obtained using a wavelength filtering component as part of the wall of channel 14 or as an additional coating on top of a photosensor array.

Figure 2:
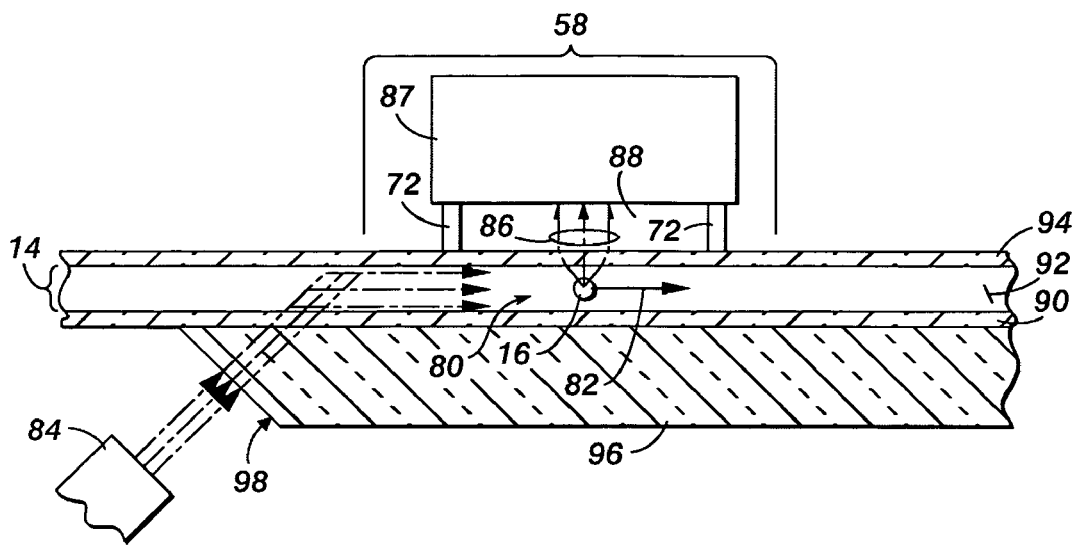
FIG. 2 is a schematic cross-sectional view of the analyzer in FIG. 1, taken along the line 2-2.

FIG. 2 shows schematically a cross-section of analyzer 10 taken along the line 2-2 in FIG. 1. Although FIG. 2 therefore shows features of second fluorescence component 58, similar features would be found in first fluorescence sensing component 56 and, to an extent, in Raman scatter sensing component 60.

As object 16 travels through portion 80 of channel 14 in the downstream direction indicated by arrow 82, it receives light from an excitation component, illustratively light source 84 which could be a laser or an LED, for example; in general, excitation radiation in any of various different energy ranges can be coupled into channel 14 to produce anti-resonant waveguiding. Portion 80 can function as an anti-resonant waveguide in response to light from source 84, or it can function in another way that provides enhanced light-target interaction. For example, other techniques that provide continuous excitation to a fluorescing molecule include tracking the molecule in motion with a scanning laser beam; using a linear array of LEDs to sustain particle excitation along its path; arranging a collimated beam along the particle path without waveguiding; and providing a Fabry-Perot-style cavity in which light passes through the medium containing the particle several times.

Sensing components using anti-resonant waveguide modes are especially advantageous in combination with fluidic devices because the fluidic channels themselves can be used as anti-resonant waveguides in various configurations. Examples of configurations include an aerosol carrying analytes in a capillary, a liquid film carrying analytes within a channel or between glass slides, etc.

In response to light from source 84, an analyte within object 16 fluoresces, emitting light with a characteristic spectrum of photon energies. A portion 86 of the light is emitted toward assembly 87, which includes at least IC 68 and possibly also other structures. Photons in portion 86 can therefore be photosensed by cells of a photosensor array on IC 68. Assembly 87 is positioned so that the photosensor array on IC 68 is close to and parallel to the path of object 16 through portion 80, to increase light collection efficiency.

The term "emanation path" or simply "path" is used herein to refer to a substantially continuous series of positions from which light may emanate, with a part of a path being referred to herein as a "segment". Segments may overlap or be included in one another. Photon emanation along a path "can vary" if it is possible for total quantities of photons emanated from different positions along the path to be measurably different.

A photosensor array is "positioned along" or "along" a path or a segment if the array is positioned near the path or segment in such a way that one or more of its photosensors can photosense light emanating from the path or segment.

Similarly, photosensor array is "positioned along" or "along" a channel or a portion of a channel if the array is positioned near the channel or portion in such a way that one or more of its photosensors can photosense light emanating from the channel or portion.

Assembly 87 is illustratively supported on spacers 72 to avoid disturbing anti-resonant waveguiding in portion 80 of channel 14. Spacers 72 are positioned outside portion 80, and, as a result, air gap 88 below assembly 87 prevents disturbance of waveguiding because air has a lower refractive index than that of the liquid within the waveguide. Any other appropriate structure could be provided that would prevent disturbance of waveguiding; examples include a gas or vacuum layer or possibly even a liquid layer or film with a low refractive index. A thin gap, layer, or film that is only a few microns thick, e.g. 10 μm, is sufficient to prevent disturbance of waveguiding if it has a sufficiently low refractive index.

Because object 16 receives excitation continuously throughout portion 80, fluorescence also occurs continuously along the photosensor array. As a result, spectral information is collected continuously as object 16 moves through portion 80. As described below, a similar technique can be used for light scattered by object 16.

The structure shown in FIG. 2 could also be used to implement Raman scatter sensing component 60 in a way that, although not comparable to dedicated Raman sensors, may provide acceptable performance and resolution with sufficient spectral range for a given application such as for specific Raman bands of interest. The output signal could indicate a set of intensity ratios of selected Raman lines and/or certain narrow intervals of a Raman spectrum rather than a complete Raman spectrum. By focusing on key differentiators in a Raman spectrum, this technique could provide the most relevant input for data analysis and comparison against a library of Raman profiles or another such database. This approach may be more tractable and efficient as a first step than comparing an entire Raman spectrum with a huge library of profiles.

To implement a Raman scatter sensing component as shown in FIG. 2, it would be necessary that light source 84 and IC 68 meet appropriate specifications, especially with regard to sensitivity and background light suppression within analyzer 10. In addition, suitable optical elements would be necessary between channel 14 and the photosensor array of IC 68 to ensure efficient and suitable light sampling.

Exemplary differences between a fluorescence sensing component and a Raman scatter sensing component would be as follows: A fluorescence sensing component could include a photosensor array in which cells photosense within a wide spectral range with rather low resolution, e.g. 400-700 nm with a moderate wavelength resolution of 2-5 nm. In contrast, a Raman scatter sensing component could include a photosensor array in which cells photosense within a smaller spectral range close to the excitation wavelength but with greater resolution, e.g. 800-830 nm with a resolution of 0.2-0.5 nm or even higher resolution. The sensing range for Raman scatter sensing must be set in accordance with typical energies of Raman scattered photons, which are 100 $cm^{-1}$ to a few 1000 $cm^{-1}$ wavenumbers different from the excitation photon energy, where wavenumber $k=2\pi/\lambda$ in units of 1/cm.

FIG. 2 also illustrates one of the ways in which support structure 12 could be implemented. Support layer 90 could, for example, be a light-transmissive glass or silicon substrate. Channel 14 can be defined in a micromolded layer 92 of polydimethylsiloxane (PDMS). PDMS is an inexpensive, biocompatible, transparent, silicon based elastomer with controllable hardness, hydrophobicity, excellent gas permeability, and surface chemistries that can be tuned to specific applications. It is sufficiently transparent in the visible portion of the spectrum to allow visualization of fluidic transport and measurements through a portion of layer 92, such as by a photosensor array on IC 68. In patterning layer 92 and other layers in FIG. 2, the length of channel 14 in which light-target interaction occurs can be chosen to minimize interference between different analytes.

Techniques for producing a patterned layer of PDMS are described, for example, in Becker, H., and Gartner, C., *Electrophoresis*, Vol. 21, 2000, p. 12, incorporated herein by reference. For example, a template can be fabricated on glass from SU-8 polymer, and PDMS can then be deposited to form a patterned structure within the template. The template can then be removed. Over layer 92 is a light-transmissive plate 94, such as glass.

The use of a patterned layer of PDMS is merely illustrative, however. A wide variety of other techniques could be used to produce microchannels or other channels suitable for analyzer 10. For example, techniques could be used that etch glass to produce channels. Also, channels could be microfabricated by patterning a layer of a polymer material such as SU-8 to produce high aspect ratio channel walls. Depending on the medium that carries analyte through channel 14, parameters of channel 14 can be modified for optimal results. If the medium is an ordinary fluid, for example, the optimal width of the channel will be different than if the medium is an aerosol. It may also be necessary to adjust the width of the channel to obtain a desired throughput.

A specific parameter of channel 14 that can have significant effects is adhesiveness of the channel wall. For example, experiments with *B. Thurengiensis* on uncoated surfaces have shown that adhesion may be a concern. This would be especially important for microfluidic channels, i.e. channels with maximum transverse inner dimensions less than 0.1 mm—their characteristically high surface area to volume ratio could lead to significant system loss. Bioadhesion could also compromise the ability to track the passage of a sample analyte through the entire length of channel 14. Bioparticles are attracted to charged or highly polarized surfaces such as glass, plexiglass acrylic, silicon, and even polymeric materials. With prolonged contact, bacteria and proteins may adhere to almost any surface by exposing more of their hydrophobic core regions, thus adapting their contact area to the specific surface properties. Once such a molecule is sufficiently close (e.g. 1-10 nm) to any surface, van der Waal's force dominates, and adhesion becomes a significant issue.

Various techniques can be used to reduce sample loss through surface adhesion, such as by providing barriers that prevent bioparticles from coming too close to the surfaces. More specifically, an anti-adhesive coating can be applied to prevent bioparticles and other analytes from sticking to the walls. Dip-coated polyethylene glycol (PEG) is a good choice for preventing adhesion of most biomaterials such as bacteria and proteins. In addition, PEG may be very well suited for microfluidic devices, since PEG can maintain capillary force on aqueous solutions. Other coatings may be viable options depending on sample properties, material interface chemistry, and operating conditions and regimes; for example, parylene C or vapor deposited tetraglyme might provide appropriate coatings. As noted above, anti-resonant waveguiding techniques can employ a channel with an inner diameter at least up to approximately 1.0 mm and possibly greater, in which case adhesion is not as great a problem and clogging is unlikely to occur; nevertheless, anti-adhesion measures may be advantageous to prevent spurious background signals emitted by material adhering to a channel's inner wall.

FIG. 2 also shows optical component 96 on the side of support layer 90 opposite PDMS layer 92. Optical component 96 provides an appropriate surface 98 through which light from source 84 can be coupled into the anti-resonant waveguide within portion 80 of channel 14. Although shown as separate layers in FIG. 2, support layer 90 and optical component 96 could instead be fabricated from a single layer of material by suitable processes.

FIG. 3 is a schematic view of an implementation of assembly 87 in which IC 68 includes photosensor array 100 and also has spacers 72 attached to it, such as after microfabrication of array 100 and other components. Photosensor array 100 is illustratively a two-dimensional array, with at least two rows of cells that include photosensors.

Different rows or other parts of photosensor array 100 can be provided with different coatings or can be otherwise structured so that their cells photosense different ranges or subranges of photon energies. As a result, the information obtained from a single IC can provide a detailed analysis of incident photons over a broad range of photon energies. In addition, reference cells, such as the cells in row 102, can be used to provide a spatially resolved real-time reference signal, such as to continuously monitor position of an object emanating light as it moves past array 100.

Within an array, a "pair" of cells is any two cells; unless otherwise specified, the cells in a pair need not have any other specific relationship to each other. The cells in a pair are "near each other" if the distance between them meets a suitable criterion for nearness, such as being no greater than ten times the maximum diameter of the larger of the cells. In general, for example, two cells that are adjacent are also near each other. More generally, a set of cells are all "nearby" another cell if each cell in the set and the other cell, taken as a pair, are near each other. A feature of array 100 is that it includes one or more reference cells that are nearby to a subrange cell, such as by being adjacent to the subrange cell.

Each cell in row 102 photosenses photons throughout a suitable range, characterized as $\lambda_{all}$, to produce a reference for a nearby cell in row 104. For implementations in which it is advantageous to have signal strengths of the same order from a cell in row 102 and its paired cell in row 104, the cell in row 102 must be different from the cells in row 104. For example, it could have a different sensing area or it could have a gray filter coating different than a coating over the paired cell in row 104.

Each cell in row 104, on the other hand, photosenses a respective subrange between $\lambda_{min}$ and $\lambda_{max}$, with illustrative cell 106 photosensing a subrange centered around $\lambda_p$. IC 68 also includes array circuitry (not shown) as well as peripheral circuitry 110 which perform various functions relating to readout of photosensed information from array 100.

Figure 3:
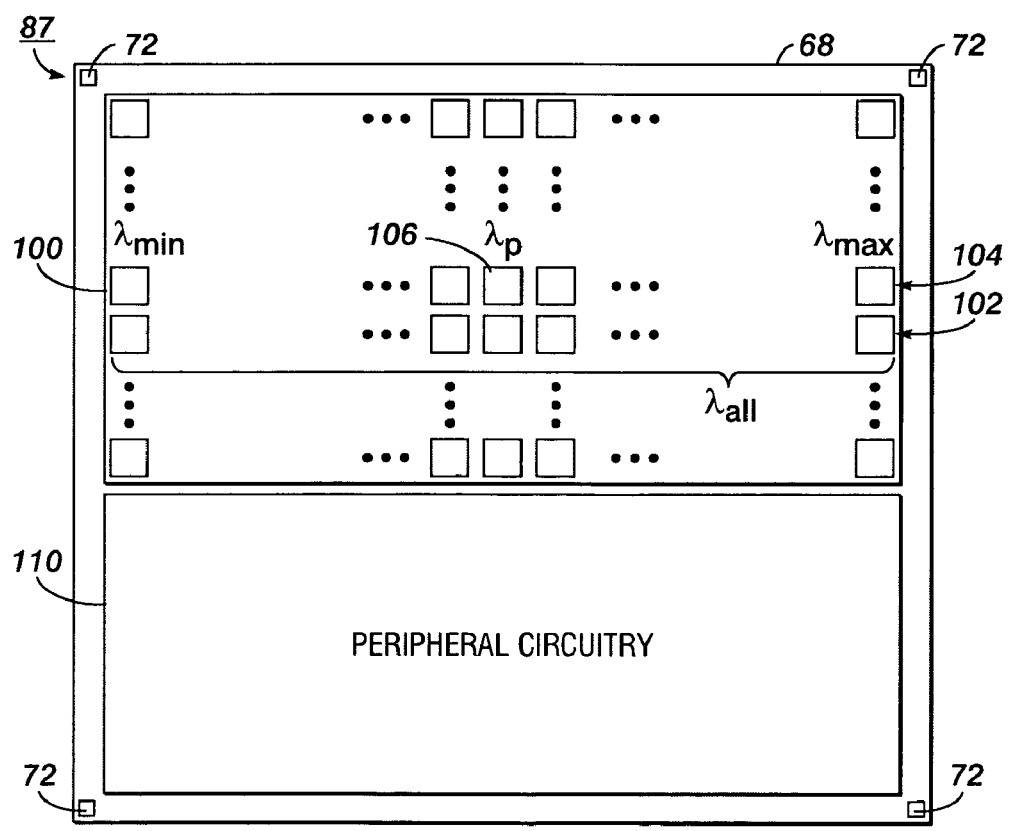
FIG. 3 is a schematic plan view of an implementation of an assembly that can be used in FIG. 2, including an integrated circuit (IC) with a photosensor array.

One advantage of the technique illustrated in FIG. 3 is that IC 68 provides a compact photosensor array that can be used for various functions within a system such as analyzer 10. The compactness of IC 68 also allows for an interactive detection scheme. Subsequent or adjacent ICs within analyzer 10 may exchange information or trigger events. The combination of analysis results from several ICs within analyzer 10 may help to obtain orthogonal information and ultimately enable reliable identification of object 16.

Figure 4:
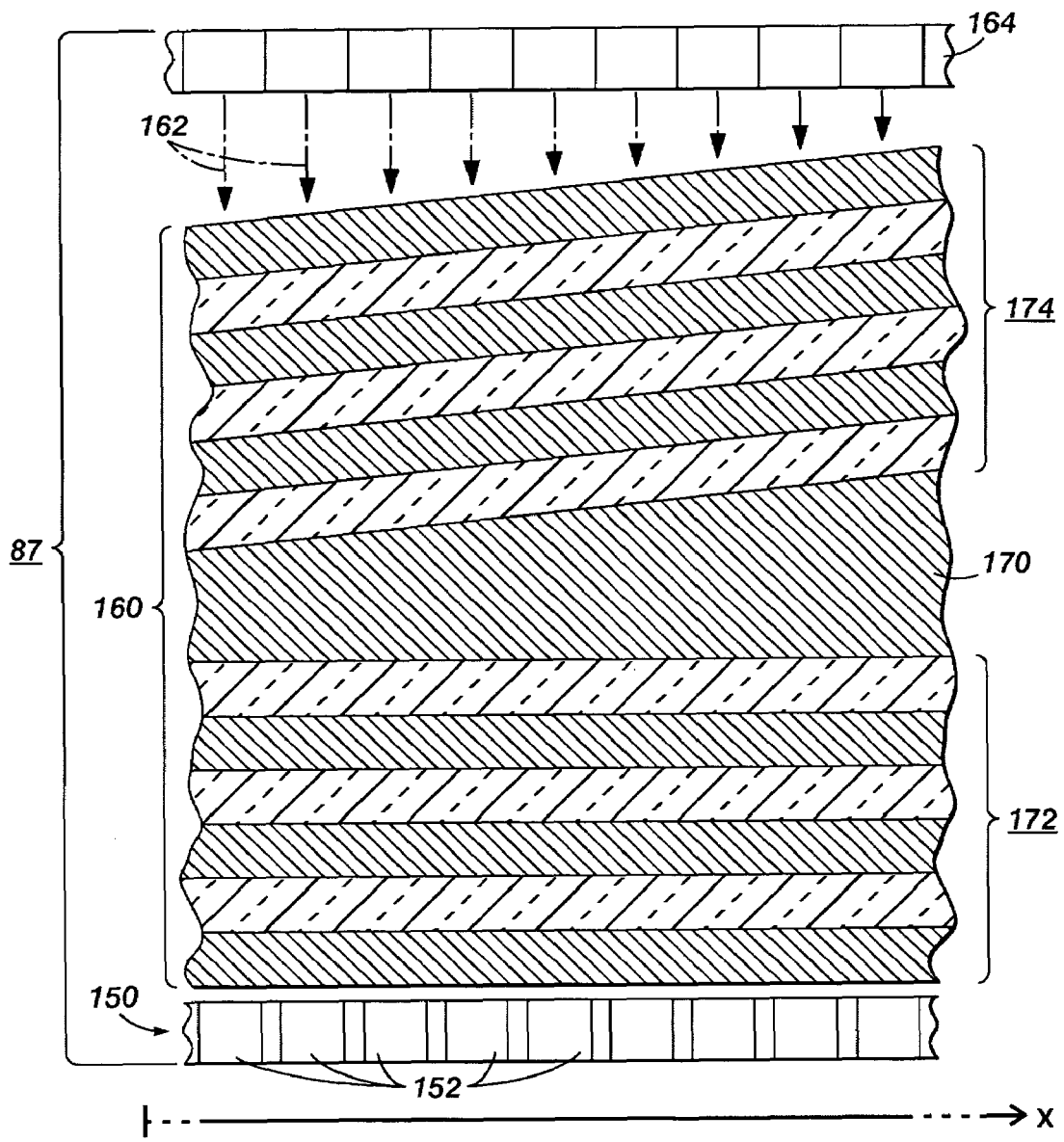
FIG. 4 is a schematic cross-sectional view of another implementation of an assembly that can be used in FIG. 2.

FIG. 4 illustrates another implementation of assembly 87, showing in greater detail how cells of an array photosense subranges, such as in row 104 in FIG. 3. As in FIG. 2, assembly 87 as in FIG. 4 can be supported over air gap 88 by spacers 72.

In FIG. 4, a cross-section has been taken through a fragment 150 of a photosensor array, with cells 152 of the fragment 150 shown schematically in cross-section. Over cells 152 is a transmission structure 160 that receives incident light 162, such as from an optional Selfoc® or other gradient index (GRIN) lens array, illustrated by lens array portion 164. Lens array portion 164 can be designed to receive light from air gap 88 as in FIG. 2 and to provide a parallel beam to structure 160, increasing spectral resolution.

A structure that "transmits" photons, sometimes referred to herein as a "transmission structure", is any material structure through which light can propagate. It is not necessary that there be a one-to-one relationship between photons that enter a transmission structure and photons that exit from it as long as the structure provides exiting photons in response to entering photons as a result of light propagation through the structure.

More generally, to "transmit" photons is to perform a function by which exiting photons at an exit position are provided in response to entering photons at an entry position as a result of light propagation between the entry and exit positions. To "transmit only" a specified set of photons from a first position to a second refers to a function that transmits photons from the first position to the second, but predominantly photons in the specified set. As with photosensing, described above, if a transmission structure transmits only a specified set of photons, between 60-90% of the transmitted photons are in the specified set, but the percentage could be lower or higher. In some applications, 90% or even 95% or more of the photons are in the specified set.

One type of transmission structure is a "coating", meaning a layered structure of light-transmissive material that is on or over another component such as a photosensor array. A coating varies "continuously" along a channel or path if the coating varies as a continuous function of its position along the path.

A transmission structure provides (and a cell receives from a transmission structure) photons "throughout", "within", or "in" a range or subrange if the provided photons are predominantly within the range or subrange. As with photosensing, described above, between 60-90% of the photons from a transmission structure typically have energies within the range or subrange, but the percentage could be lower or higher. In some applications, 90% or even 95% or more of the photons have energies within the range or subrange.

Transmission structure 160 can, for example, be a film with laterally varying light transmission properties as described, for example, in co-pending U.S. patent application Ser. No. 10/922,870, entitled "Chip-size Wavelength Detector" and incorporated herein by reference in its entirety. In the portion of transmission structure 160 shown in FIG. 4, wedge-shaped transmissive cavity 170 is enclosed between reflective films 172 and 174, forming a wedge-shaped Fabry-Perot etalon. Because its thickness varies as a function of position along the x-axis, transmission structure 160 will transmit different wavelengths as a function of position along the x-axis.

Transmission structure 160 can be produced with appropriate coatings on or over a photosensor array. Films 172 and 174 and cavity 170 could all be produced, for example, by exposure to deposition beams in an evaporation chamber; films 172 and 174 with uniform thicknesses could be produced by appropriate on-axis deposition, while cavity 170 with laterally varying thickness can be produced by appropriate off-axis deposition. FIG. 4 illustratively shows films 172 and 174 as relatively thick compared to cavity 170, which would be appropriate for layers of non-metallic material such as $SiO_2$, $TiO_2$, or $Ta_2O_5$, with thicknesses designed as described below; such materials are typically used to produce Bragg mirrors by depositing thin alternating layers with low absorption coefficients and large differences in refractive indices. If films 172 and 174 are reflective metal, however, they could be much thinner.

For an implementation with non-metallic material, specific thicknesses of cavity 170 and films 172 and 174 could be designed from the desired transmitted wavelength $\lambda$ and the refractive index n of cavity 170. The thickness of cavity 170 is typically chosen to be $\lambda/(2n)$ or an integer multiple thereof, while the thicknesses of Bragg mirror layers within films 172 and 174 are typically $\lambda/(4n)$. The number of pairs of such layers in each of films 172 and 174 can vary between a few (e.g. 2-5) all the way up to 20 or 30, depending on the difference in refractive index between the two materials used, the desired transmission band width, and the desired stop band reflectivity. Therefore, in typical implementations, films 172 and 174 are much thicker than cavity 170, as suggested in FIG. 4.

Figure 5:
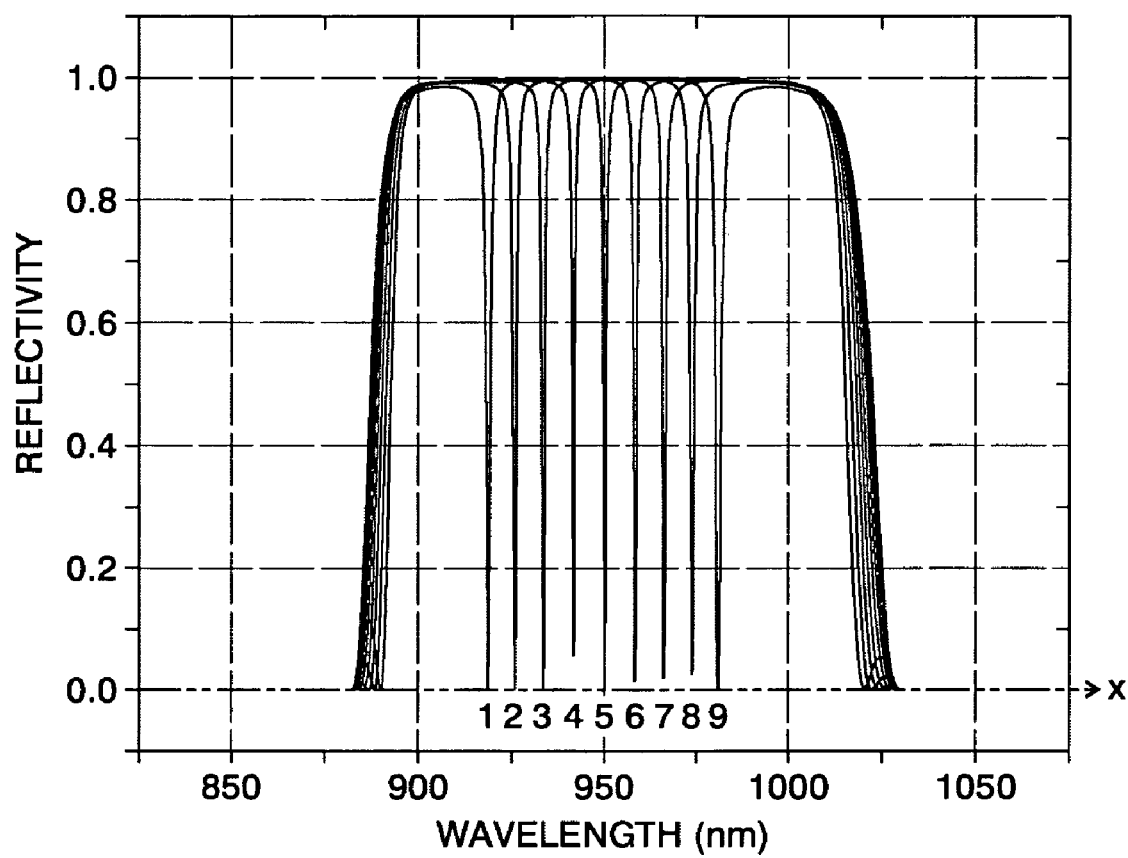
FIG. 5 is a graph illustrating laterally varying light transmission properties of a transmission structure in FIG. 4.

FIG. 5 illustrates the laterally varying light transmission properties of transmission structure 160. Because its thickness varies as a function of position along the x-axis, cavity 170 transmits different wavelengths as a function of position along the x-axis. Wavelengths of photons predominantly transmitted to nine of cells 152 as in fragment 150 are illustrated by the low reflectivity minima labeled 1 through 9. As can be seen, the high-transmissivity photon energy range for transmission structure 160 varies laterally.

FIG. 6 illustrates another implementation of assembly 87, with features that have the same reference numbers as in FIG. 4 being implemented as described above. Rather than transmission structure 160, however, assembly 87 includes transmission structure 180. Transmission structure 180 can, for example, be a laterally graded Bragg mirror in which each of layers 182, 184, 186, and 188 is laterally graded. Each of layers 182, 184, 186, and 188 could be produced as described above for cavity 170, using off-axis deposition in an evaporation chamber.

FIG. 7 illustrates the laterally varying light transmission properties of transmission structure 180. Because its thickness varies as a function of position along the x-axis, transmission structure 180 reflects different wavelengths as a function of position along the x-axis. Curves 200, 202, 204, and 206 are shown, representing reflectivity of the portion of transmission structure 180 over each of four cells 152 in fragment 150, with curve 200 being for the leftmost cell of the four in FIG. 6 and curve 206 being for the rightmost cell of the four. As can be seen, the high-reflectivity photon energy range for transmission structure 180 varies laterally.

Figure 8:
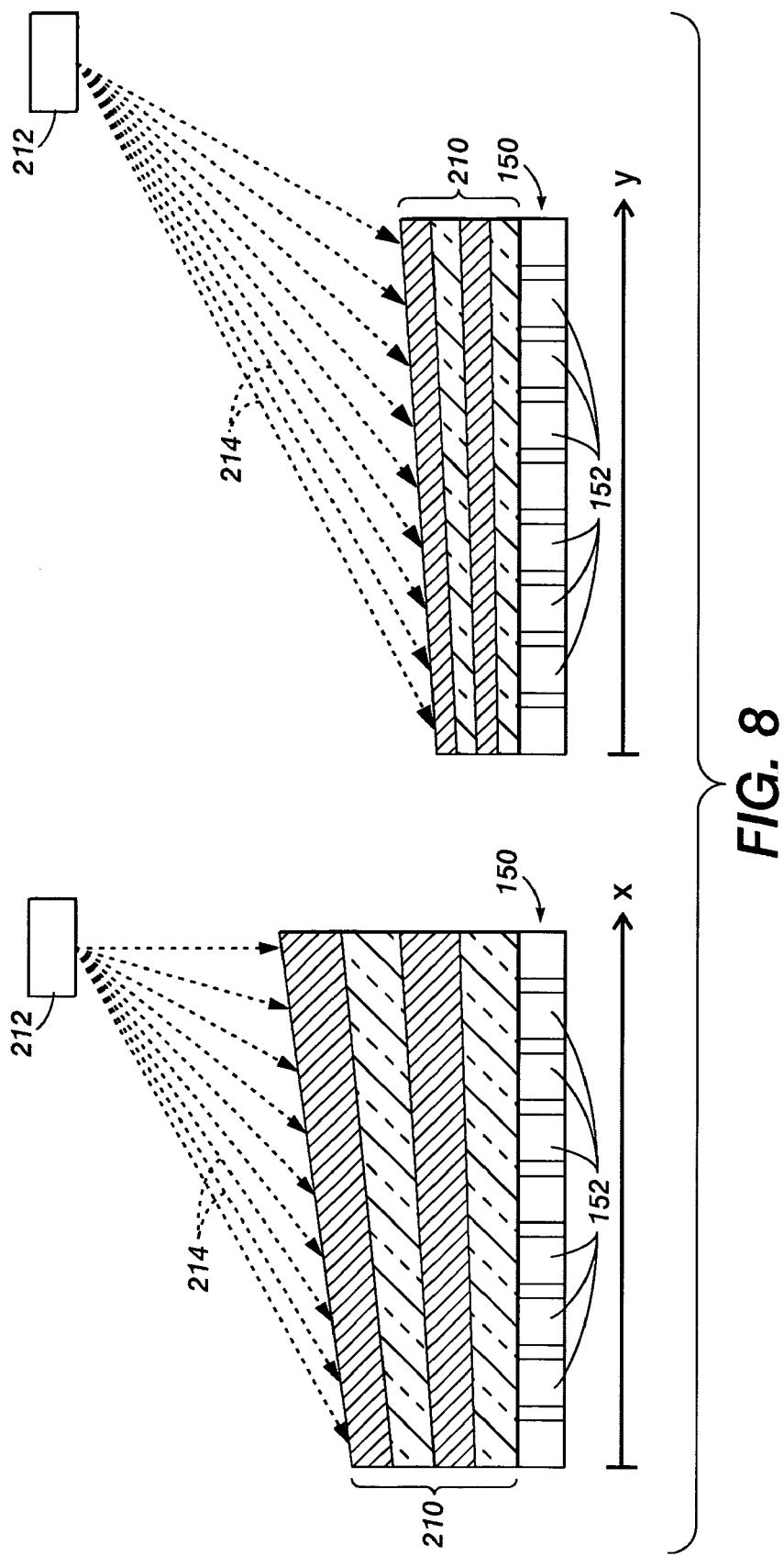
FIG. 8 illustrates a technique that produces a transmission structure that can be used in an assembly as in FIG. 2, showing orthogonal schematic cross-section views of deposition.

FIG. 8 illustrates a technique that produces transmission structure 210 with laterally varying light transmission properties similar to those illustrated in FIGS. 5 and 7 but with lateral variation in each of two dimensions. This technique can be used to produce different coatings for different rows of a photosensor array so that their cells photosense different ranges or subranges of photon energies, and can be used separately or in combination with reference cells.

Transmission structure 210 is produced on or over cells 152 of photosensor array 150 by using deposition source 212 to provide deposition beam 214 that can be characterized at any given point on the surface of structure 210 by two angles. One of the two angles results from angular variation of deposition beam 214 in the x-direction across array 150, while the other results from angular variation in the y-direction. As a result, the thickness gradient of structure 210 is similarly different in the x- and y-directions. Therefore, cells within each row extending in one of the two directions will photosense a range of photon energies similarly to FIG. 7, but the range will be different than the range photosensed by cells in any other row extending in the same direction.

The technique of FIG. 8 could be implemented in a variety of ways. For example, during deposition, structure 210 could be formed on a support structure that is tilted as required, deposition source 212 could be tilted as required, or both kinds of tilt could be employed.

Figure 9:
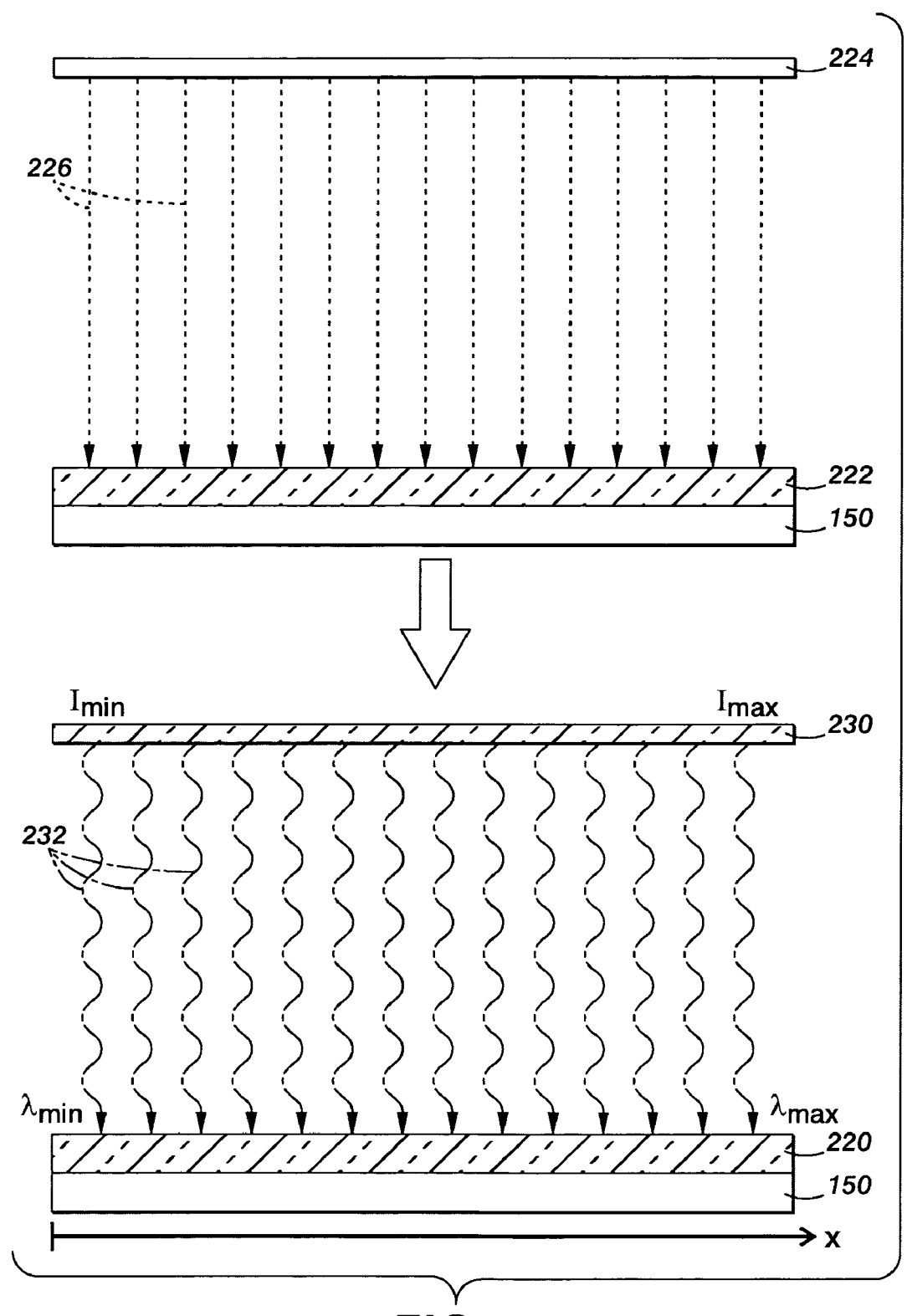
FIG. 9 illustrates another technique for producing a transmission structure that can be used in an assembly in FIG. 2, showing two schematic cross-section views of stages of the technique.

FIG. 9 illustrates a technique that produces transmission structure 220 with laterally varying light transmission properties similar to those illustrated in FIGS. 5 and 7 but without variation in thickness of transmission structure 220. The technique in FIG. 9 can be characterized as providing laterally varying optical thickness d*n, where d is thickness and n is index of refraction, but without actual variation in thickness d. In contrast, the techniques of FIGS. 4-8 provide varying optical thickness by providing actual variation in thickness.

In the upper part of FIG. 9, homogeneous coating 222 is deposited by deposition source 224, which provides deposition beam 226 uniformly over the surface of photosensor array 150 similar to those in FIGS. 4, 6, and 8. This operation could, for example, be implemented with conventional deposition techniques.

Then, in the lower part of FIG. 9, light source 230 provides radiation 232 that is scanned across the coating over array 150 to introduce a laterally varying change of refractive index in resulting transmission structure 220. For example, source 230 can be an ultraviolet source that provides intensity I with a constant value along each line parallel to the y-axis (perpendicular to the plane of FIG. 9), but varying from $I_{min}$ for lines nearer the y-axis to $I_{max}$ for lines farther from the y-axis, as shown in FIG. 9 by the values along the x-axis. As a result, the wavelengths transmitted to cells in array 150 can vary along the x-axis from $\lambda_{min}$ to $\lambda_{max}$, as shown. The same pattern of intensity can be concurrently applied by source 230 to each of a number of arrays that are appropriately arranged, allowing batch fabrication of arrays. Two-dimensional variation in optical density equivalent to that in FIG. 8 could also be obtained with two-dimensional variation in the ultraviolet source's intensity.

The techniques illustrated in FIGS. 4-9 could be implemented in various other ways, with different cells of a photosensor array photosensing slightly different subranges of a range of photon energies. For example, additional details about various production and calibration techniques and characteristics of transmission structures that could be employed are described in co-pending U.S. patent application Ser. No. 10/922,870, entitled "Chip-size Wavelength Detector" and incorporated herein by reference in its entirety. Also, co-pending U.S. patent application Ser. No. 11/316,241, entitled "Photosensing to Obtain Information From Photon Energies" and incorporated herein by reference, describes a step-like transmission structure that could be used.

If quantities photosensed by the cells are read out in parallel, spectral information about incident photons is obtained. As illustrated in FIG. 3, nearby cells, such as in a parallel row, can photosense quantities of photons throughout the range of photon energies to provide reference information. If adjacent cells in the array have overlapping subranges, computational techniques such as deconvolution can be used to improve accuracy.

In general, the resolution of a technique as in any of FIGS. 4-9 depends heavily on the number of cells in an array, the full width half maximum (FWHM) of the transmission peak, and the peak shift per cell. The smaller the FWHM and the peak shift, the better the resolution. On the other hand, the totally covered spectral width can be enhanced by increasing the FWHM and the peak shift per cell. Therefore, the technique can be customized to the needs of a specific application. For example, the use of a Fabry-Perot cavity as in FIG. 4 enables very high spectral resolution, while a version with multiple cavities and many layers as in commercially available products will be favorable for applications with low light intensities in combination with small spectral resolution such as with fluorescence. With such an approach, the spectral width of the transmission window and the reflectivity of the stop band can be optimized separately, which may be advantageous because the reflectivity of the stop band determines stray light suppression. It would also be possible to use a single laterally graded distributed Bragg reflector (DBR) mirror as in FIGS. 6 and 7 to obtain a photosensor array with high light sensitivity but limited wavelength resolution, appropriate for fluorescence or luminescence sensing.

In a version with only one DBR mirror with slightly graded transmission properties as in FIGS. 6-8, integrated over a photodiode array for example, the photocurrent in each cell is slightly different from its neighbors depending on the incident light spectrum. If the transmission properties of the DBR over each cell are known, the original spectrum of incident light can be reconstructed. The number of cells defines the number of spectral points that can be reconstructed and therefore determines spectral resolution. The reconstruction works best for wavelengths where transmission changes drastically from one cell to the next. Therefore, this technique could be used to resolve wavelengths at the edges of the DBR mirror. The DBR mirror could be positioned in such a way that the side edges on one side cover the spectral region being analyzed. Multiplication of the resulting photocurrent with a matrix that contains the transmission function of the DBR mirror provides a reconstruction of the incident light spectral distribution.

Resolution can be improved by positioning DBRs on a second row of the photodiode array so that the opposite edge of the reflectivity plateau overlaps the spectral range of interest. Once again, to evaluate the data, the total light intensity distribution must be known for all cells, which can be obtained from a third row of pixels without any DBRs.

A particular advantage of analyzer 10, when implemented with techniques similar to those of FIGS. 3-9, is that spectral information of objects can be collected step-by-step as the objects move across or along a series of sensing components, each of which obtains information about a respective range of photon energies. As a result, highly sensitive optical characterization techniques can be combined, including multiple range fluorescence spectroscopy and Raman spectroscopy, as described above in relation to FIG. 1. Each of sensing components 56, 58, and 60 can be thought of as a chip-size spectrometer that includes a photosensor array together with a laterally varying filter such as a coating. The laterally varying transmission and reflection properties of the coating over the photosensor array define a correlation between position and photon energy. Therefore the spatially dependent signal from the photosensor array contains information about the incident spectrum. Because of the distributed nature of the spectrometer and the fact that the incident light traverses the photosensor array in the process of resolving spectral distribution, sensitivity is improved, making additional optics unnecessary.

Relative movement between an object and a photosensor array can be obtained in various ways, such as by moving one or both of the object and the array. Movement of an object can be guided in various ways, including by falling through a funnel under gravitational acceleration; by being injected into a well-defined stream of air, liquid, or other particles; or by being guided by a tube, capillary, or similar aperture.

In general, high sensitivity is obtained by the above techniques because the light from the object is received at any given time by only a few cells with relatively narrow subranges. But by photosensing light emanating from an object or another optical signal across the entire array, information about a complete range of photon energies can obtained. This technique therefore allows longer integration times than conventional techniques but does not sacrifice throughput capacity. Sensitivity can be adjusted by selecting the size and number of cells assigned to a specific subrange of photon energies. Simpler optics can be used and no dispersion element is necessary. Note that in conventional spectrometers, any light that is diffracted into the $0^{th}$, $2^{nd}$, and higher orders is wasted.

In experimental implementations, a coating as in FIG. 4 typically transmits approximately 60% of photons in its respective subrange. The subranges can be chosen with wavelengths that span between 0.01 and tens of nanometers (nm), depending on the design and gradient of the coating and the cell size of the photosensor array. Very high light yield can be achieved by using a highly sensitive photosensor, such as an avalanche photosensor array.

In contrast to transmission structures 160, 180, 210, and 220, any coating or other transmission structure over row 102 in FIG. 3 must function as a gray filter across the range $\lambda_{all}$ in order to provide a suitable reference. It may also be possible to leave row 102 uncoated in some implementations.

Figure 10:
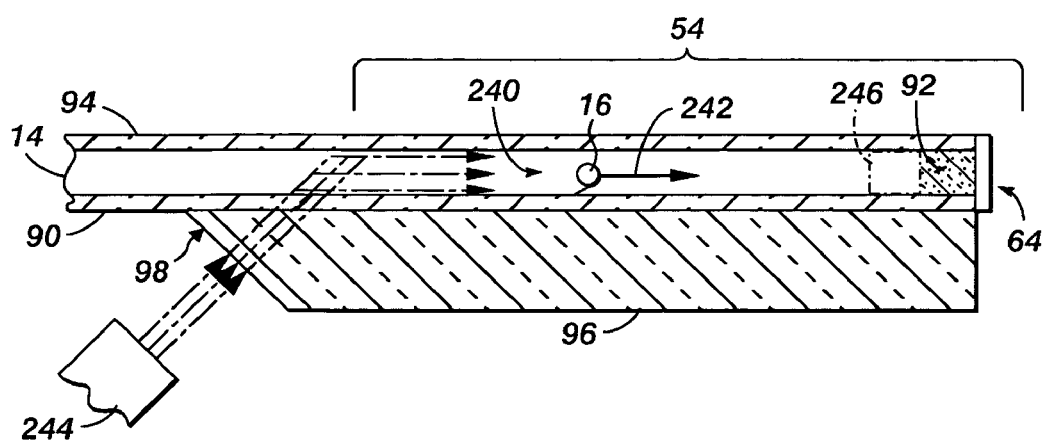
FIG. 10 is a schematic cross-sectional view of the analyzer in FIG. 1 taken along the line 10-10.

FIG. 10 shows schematically a cross-section of analyzer 10 taken along the line 10-10 in FIG. 1. FIG. 10 therefore shows several features of optical absorption sensing component 54, including IC 64, which is shown by itself, but would be implemented within an assembly, such as any of the implementations of assembly 87 as described above.

As object 16 travels through portion 240 of channel 14 in the downstream direction indicated by arrow 242, it receives light from an excitation component, illustratively light source 244 which is a suitable broadband illumination component such as a white light source and which could be an LED or a halogen lamp. As in FIG. 2, portion 240 can function as an anti-resonant waveguide in response to light from source 244, or it can function in another way that provides enhanced light-target interaction, as described above.

In response to light from source 244, object 16 scatters or absorbs light, resulting in a modified spectral distribution of transmitted light photosensed by cells of a photosensor array on IC 64. For example, object 16 may contain an analyte that absorbs photons within certain energy subranges, producing an absorption spectral distribution. Because object 16 receives excitation continuously throughout portion 240, cells on IC 64 will continue to photosense the absorption spectral distribution as object 16 passes through portion 240 of channel 14. Then, the spectral distribution will return to its unmodified form when object 16 exits from sensing component 54 through curved portion 246 of channel 14.

Figure 11:
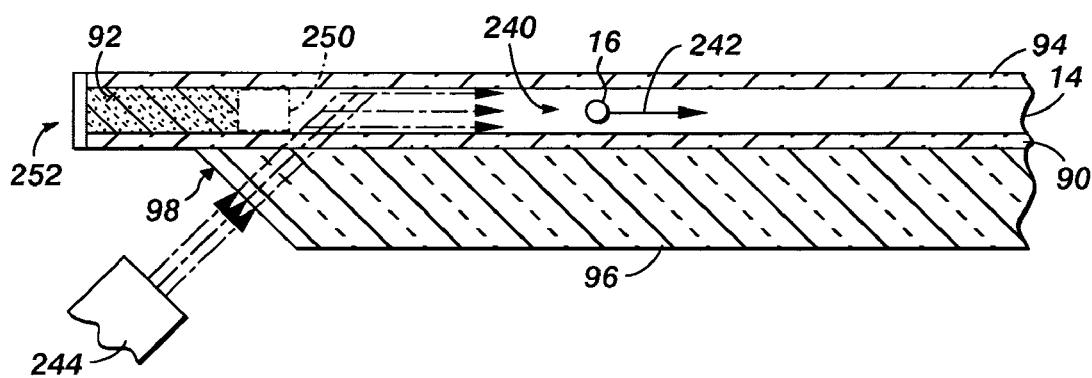
FIG. 11 is a schematic cross-sectional view similar to that of FIG. 10 for a backscatter sensing component.

FIG. 11 shows schematically a cross-section of analyzer 10 taken along a line similar to that of FIG. 10 but through a Raman backscatter sensing component. As suggested by the reference numerals that are the same as in FIG. 10, many features of FIG. 11 are implemented the same as in component 54. For example after entering through curved portion 250 of channel 14, object 16 travels through portion 240 in the downstream direction indicated by arrow 242 and receives light from an excitation component, illustratively light source 244 as in FIG. 10. Portion 240 can function to provide enhanced light-target interaction, as described above.

In response to light from source 244, object 16 (or an analyte in it) performs Raman scattering of light in an upstream direction, referred to herein as backscattering. The backscattering results in a modified spectral distribution photosensed by cells of a photosensor array on an IC within assembly 252, illustratively positioned at the upstream end of portion 240 of channel 14, but alternatively positioned outside the downstream end if source 244 illuminates portion 240 from the downstream end. Assembly 252 could be implemented with any appropriate structure, including the above-described implementations of assembly 87. Because object 16 receives excitation continuously throughout portion 240, cells on the IC in assembly 252 will continue to photosense the backscattered spectral distribution as object 16 passes through portion 240 of channel 14. Then, the spectral distribution will return to its unmodified form as object 16 exits from the sensing component. As shown, the photosensor array of the IC in assembly 252 covers the whole end facet of channel 14, including the channel walls; this is necessary because backscattered light may not only propagate freely through liquid in channel 14 but may also be guided within the walls surrounding the liquid, such as in layer 90 and plate 94.

FIG. 12 illustrates a variation on FIGS. 10 and 11. The technique of FIG. 12 can be used, for example, where channel 14 has an inner diameter less than 30 μm or is otherwise so small or so structured that light is not satisfactorily distributed over IC 64 and the IC in assembly 252 when attached directly to an end facet of channel 14 as in FIGS. 10 and 11. In such situations, in addition to an alignment problem, the cells of the photosensor array cannot be made sufficiently small to allow a satisfactory number of cells to obtain the desired wavelength resolution from the light received from channel 14 and its walls, including layer 90 and plate 94. Therefore, prism 260 can be positioned to diffract light that emerges from the end facet. The diffracted light can then be photosensed by cells of array 262, with different cells photosensing different photon energy subranges as a result of diffraction. For example, ray 264 represents shorter wavelengths, ray 266 represents intermediate wavelengths, and ray 268 represents longer wavelengths, with each ray being detected by a different cell of array 262.

IC 64, the IC in assembly 252, and an IC that includes array 262 could each be implemented with the techniques described above in relation to FIGS. 3-9. For example, cells in row 102 of photosensor array 100 could provide reference information for use in correcting position-dependent inhomogeneities resulting from characteristics of channel 14.

FIG. 13 illustrates exemplary operations in producing an analyzer like analyzer 10 in FIG. 1. In particular, the operations in FIG. 13 make it possible to produce apparatus in which relative movement between an optical signal and a photosensor array can be produced, and in which, for different segments of the optical signal's path across the array, respective sets of cells photosense within different respective subranges of photon energy.

The operation in box 270 in FIG. 13 produces a fluidic structure with a channel in which objects can be carried by fluid. For example, the operation in box 270 could include manufacturing a fluidic structure by positioning or otherwise producing a structured spacer layer between two quartz slides. The spacer layer could be a patterned layer of PDMS, produced as described above in relation to FIG. 2, or could be any other suitable material or combination of materials, including, for example, Gelfilm® or quartz. The operation in box 270 could alternatively be implemented in various other ways, such as by defining a fluidic channel in a quartz slide by glass etching or by molding PDMS to produce a channel, and by then combining the resulting structure with an upper quartz slide. In another alternative, two layers of PDMS could be fabricated on separate substrates and then one could be flipped over and aligned with the other by chip-on-chip assembly. Also, a final substrate of glass, PCB, or PDMS or sufficient hardness could be used to allow direction connection to control and detection measurement circuitry.

The operation in box 272 then attaches fluidic components to the fluidic structure produced in box 270. The fluidic components attached in box 272 can include, for example, connectors, tubing, pumps, sensors and so forth. An important function of the fluidic components attached in box 272 is that they can be operated to cause and control movement of objects in the channel. The operation in box 272 can also include attaching wires or other appropriate circuitry to provide signals from a microprocessor or input/output (I/O) device to pumps and other fluidic components.

The operation in box 274 attaches components for enhanced light-target interaction. In the implementation described above in relation to FIGS. 1 and 2, for example, the operation in box 274 can attach optical component 96 on the side of support layer 90, providing an appropriate surface through which light can be coupled into a portion of channel 14 that functions as an anti-resonant waveguide. Similarly, the operation in box 274 can produce spacers 72 to provide a suitable gap that avoids interference with anti-resonant wave guiding. For other techniques to produce enhanced light-target interaction, other suitable components can be attached to the fluidic structure.

The operation in box 280 attaches photosensor arrays with cells that photosense in different subranges. The operation in box 280 can be implemented by attaching a structure like any of the above-described implementations of detector 87. The detector can also include reference cells, which could be produced as described in more detail in co-pending U.S. patent application Ser. No. 11/316,438, entitled "Photosensing Throughout Energy Range and in Subranges", and incorporated herein by reference in its entirety. The operation in box 280 can also include attachment of wires or any other appropriate form of circuitry such as to provide power and permit a microprocessor or I/O device to read out information from the cells of each photosensor array.

The operation in box 282 can be performed at a different time, as suggested by the dashed line. For example, it could be performed in box 274, or it could be done later, because it is necessary more for operation of the analyzer than for its production. Like the detector, each light source can be attached once, after which it is stationary. In the operation in box 282, one or more light sources are positioned to produce excitation of objects being carried within the channel. For example, the operation in box 282 could include attaching and/or aligning a laser, an LED array, or other light source so that its light is coupled into a portion of the channel functioning as an anti-resonant waveguide. The operation in box 282 can also include attaching wires or other appropriate circuitry to provide signals from a microprocessor or I/O device to light sources.

The technique of FIG. 13 could be modified in many ways within the scope of the invention. For example, the operations in boxes 272, 274, 280, and 282 could be combined in any appropriate way to facilitate attachment of components in a desired sequence. Also, an additional operation could be performed to align or attach interconnects between ICs, gates, and other circuitry, such as connectors to a microprocessor or computer, or this operation could be partially performed in each of boxes 272, 274, 280, and 282. Furthermore, the technique of FIG. 13 is extremely general, and could be employed to produce a wide variety of different fluidic structures with enhanced light-target interaction, detectors, and relative movement of objects that emanate light. The example illustrated in FIGS. 1 and 2, above, shows how objects carried through a channel can pass through a series of sensing components, each of which includes a respective detector with its own photosensor array, but various other arrangements are possible, examples of which are described below.

FIG. 14 shows an alternative arrangement that could be produced by an implementation of FIG. 13, with components similar to those described above in relation to FIG. 1 having the same reference numerals. As in FIG. 1, first and second fluorescence sensing components 56 and 58 are next to each other in the series of sensing components along channel 14. In addition, however, they are positioned so that IC 290 can be attached over both of them. As a result, the photosensor array of IC 290 includes both cells along channel 14 within component 56 and also cells along channel 14 within component 58. In other respects, the operation of IC 290 can be the same as described above.

FIG. 15 is a cross-section along the line 15-15 in FIG. 14, and shows how detector 292 which includes IC 290, can be supported over air gap 88 by spacers 72 in the same manner described above in relation to FIGS. 1 and 2. In general, detector 292 can include any of the features described above in relation to FIGS. 3-9, but the lateral variation in optical thickness of the transmission structure may be such that the ranges and subranges photosensed within sensing component 56 are different from those photosensed within sensing component 58; alternatively, the ranges and subranges could be the same. An additional important feature is that spacers 72 can help to reduce cross-talk between components 56 and 58 because spacers 72 can be shaped and positioned to act as light-absorbing walls between the two components. In other words, those of spacers 72 that are between components 56 and 58 prevent photons emanating from channel 14 underneath component 56 from propagating to cells of component 58 and vice versa.

FIG. 16 shows an alternative arrangement in which detector 292 as in FIG. 15 is positioned over a set of parallel channels 294, which could be produced by producing walls 296 to subdivide a larger channel into subchannels. An advantage of the technique illustrated in FIG. 16 is that several streams of objects can be analyzed in parallel in order to increase throughput or specificity of an analyzer. As mentioned above in relation to FIGS. 14 and 15, laterally varying optical thicknesses of a transmission structure can be produced so that a different range of photon energies is photosensed in each of channels 294, or different subranges are photosensed in different channels, or the same ranges and subranges could be photosensed in all channels.

FIG. 17 shows an alternative arrangement that could be produced by an implementation of sensing component 58 in FIG. 2, with components similar to those described above in relation to FIG. 2 having the same reference numerals. As in FIG. 2, portion 80 of channel 14 functions as an anti-resonant waveguide in response to light from source 84. Assembly 87 is along portion 80, separated from plate 94 by spacers 72. Upstream from portion 80 (but downstream from light source 84) can be positioned a series of triggering photodetectors, with photodetector 300 on spacers 302 illustratively representing the series. Alternatively, another type of detector could be used, such as a Coulter counter or Mie scatter sensor.

Within portion 80, fluorescing objects 310, 312, and 314 are being carried through channel 14. As they fluoresce, objects 310, 312, and 314 emanate photons, represented respectively by rays 320, 322, and 324. As described in greater detail below, quantities read out from a photosensor array in detector 87 can be used to obtain information about objects 310, 312, and 314 even though all three objects are concurrently traveling past the array.

Figure 18:
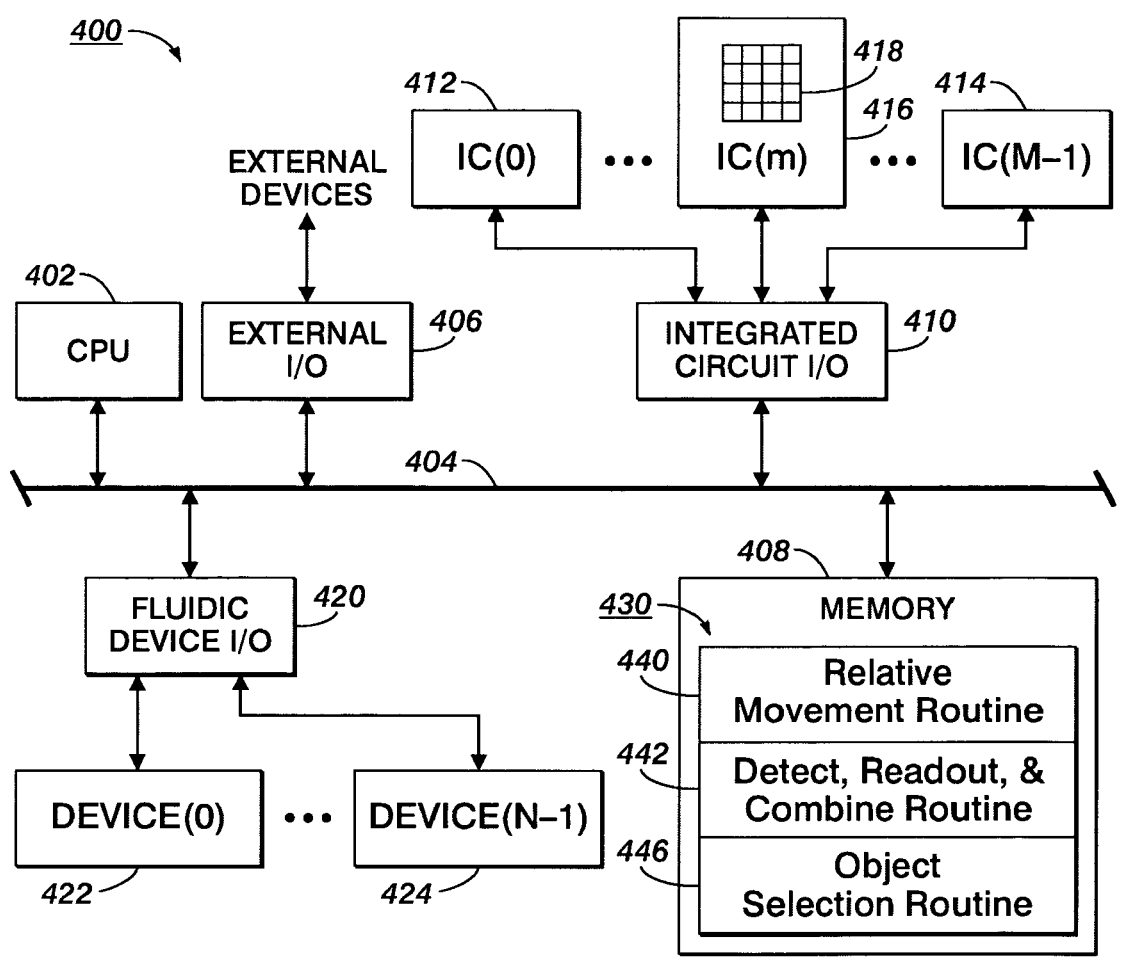
FIG. 18 is a schematic block diagram of a system that can control the analyzer of FIG. 1.

FIG. 18 illustrates system 400, an exemplary system that could be used to operate analyzer 10. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402.

System 400 also includes external input/output (I/O) component 406 and memory 408, both connected to bus 404. External I/O 406 permits CPU 402 to communicate with devices outside of system 400.

Additional components connected to bus 404 are within or connected to analyzer 10. In the illustrated implementation of system 400, IC I/O 410 is a component that permits CPU 402 to communicate with ICs in analyzer 10, such as the various ICs, photo detectors, and other sensing components described above; M ICs are illustrated in FIG. 18 by a series extending from IC(0) 412 to IC (M-1) 414. ICs 412 through 414 illustratively include IC(m) 416 with a photosensor array 418, which includes cells that photosense subranges as described above. Similarly, fluidic device I/O 420 is a component permitting CPU 402 to communicate with various fluidic devices such as pumps, metering electrodes, smart gates and other devices for gating and bifurcating, valves, flow or pressure sensors, and so forth; N fluidic devices are represented in FIG. 18 by device (0) 422 through device (N-1) 424. Such devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include relative movement routine 440, detect, readout, and combine routine 442, and object selection routine 446. In addition, program memory 430 can also store a number of subroutines (not shown) that CPU 402 can call in executing routines 440, 442, and 446.

CPU 402 executes relative movement routine 440 to communicate with fluidic devices 422 through 424. For example, CPU 402 can receive signals from sensors, perform computations to determine what fluidic operations are necessary, and then provide signals to activate pumps, metering electrodes, gates, and valves to produce appropriate relative movement between objects in channel 14 and photosensor arrays along channel 14.

In executing routine 442, CPU 402 can illustratively call a subroutine implemented as shown in FIG. 19, which could instead be within routine 442. The subroutine in FIG. 19 can be implemented for single objects moving past arrays or for spaced multiple objects moving past arrays, provided the spacings between objects are sufficient to avoid interference. Also, the subroutine in FIG. 19 follows a general strategy of performing a series of readout operations, after which spectral information is combined and provided, although it would also be possible to provide the information from each readout operation immediately.

When CPU 402 executes the operation in box 480, it performs a pre-sensing readout. The purpose is to obtain information necessary to later perform a sensing readout. The information could be obtained, for example, from a series of photodetectors illustrated by photodetector 300 in FIG. 17 or from reference cells in the photosensor array, such as the cells in row 102 in FIG. 3. It would also be possible to modify the photosensor array to include trigger cells positioned along channel 14 upstream from a line of subrange cells, and uncoated so that they provide information about all photon energies.

Using the information from box 480, CPU 402 can obtain information about each object and determine an appropriate sensing period for each object, in the operation in box 482.

For example, CPU 402 could perform calculations to determine whether one or more objects are present, the position of each object, and the speed of each object. Using this information and taking into account previously calculated sensing periods for the same objects, if any, CPU 402 can also determine an appropriate sensing period to be used during sensing readout; in general, the sensing period must provide an integration time shorter than the time necessary for an object to pass each subrange cell. Each object can therefore have a unique sensing period. Alternatively, CPU 402 could provide signals to adjust fluid speed to obtain the same result.

CPU 402 can then perform the sensing readout operation, in box 484. This operation includes providing signals so that photons are photosensed cumulatively during the sensing period obtained in box 482, and may also include signals to peripheral circuitry on an IC so that analog quantities photosensed by subrange cells are adjusted based on analog quantities sensed by paired reference cells. After adjustment, if any, analog quantities can be converted to digital signals for readout. The operation in box 484 can be implemented in whatever manner is appropriate for a given IC, whether a CCD or CMOS implementation, and regardless of whether readout is purely serial or is also parallel.

The photosensed quantities read out in box 484 can also be digitally adjusted by CPU 402 before being stored for each object, in box 490. The digital adjustment can include adjusting quantities photosensed by subrange cells based on quantities photosensed by paired reference cells, and can also include any necessary adjustments due to differences in sensing periods or other factors. The digital adjustment in box 490 and the analog adjustment, if any, in box 484 can employ the techniques described in co-pending U.S. patent application Ser. No. 11/316,438, entitled "Photosensing Throughout Energy Range and in Subranges", and incorporated herein by reference in its entirety. The position and speed information about each object from box 482 can be used to determine which photosensed quantities result from photons emanating from each object.

In performing the operations in boxes 482 and 490, CPU 402 can employ data structures (not shown) stored in memory 408. For example, one data structure can store each object's previously calculated position and speed, which can then be used in performing subsequent calculations to identify the same object. Also, a readout data structure can be employed to hold all of the adjusted quantity information about each object. The operation in box 490 can update the readout data structure each time it obtains additional information about the same object. In an implementation as in FIG. 18, the operations in boxes 480, 482, 484, and 490 can be performed separately for each of ICs 412 through 414. Further, as suggested by the dashed line from box 490 to box 480, the same operations can be performed repeatedly for each of the ICs. If the objects can be correctly identified throughout channel 14, the readout data structure can be used to hold all of the information obtained from all ICs.

Between consecutive executions of the operations in boxes 480, 482, 484, and 490, each object's optical signal may move only a few cells along the photosensing path, and consecutive objects must be sufficiently separated to avoid confusion. For example, each object may be a few µm in diameter, each pixel may have a length along the photosensing path of between 10 and 20 µm, and consecutive objects may be two or three cell lengths apart. For larger objects or for cells of different sizes, the spacing between consecutive objects can be adjusted appropriately.

Although described in relation to the implementations in FIGS. 1-17, the operations in FIG. 19 could be modified for other implementations. For example, rather than being spaced apart as shown in FIG. 17, objects could be closer together. Even if several objects are emanating photons to the same cell at the same time, it may be possible to perform computational algorithms to separate the signals of the objects. Similarly, if objects are very close to each other but positioned along different cells, an optical structure between channel 14 and detector 87 could ensure that photons emanating from different objects travel to different cells; in this way, a continuous stream of objects could be measured. Furthermore, techniques as described above could be applied to a continuous fluidic stream without distinguishable objects in it, in which case the optical signal emanating from the stream would be determined by concentrations of molecules in each position in the stream rather than by the optical signals from distinguishable objects. In effect, the stream would be divided into imaginary small volumes, each of which could be analyzed as if it were an object, allowing for continuous monitoring of how an optical signal from the fluid changes with time, such as due to changing composition of the fluid.

As can be understood, only a small fraction of an application's range of photon energies is photosensed and stored at a time by the operation in box 490. As the operations in boxes 480, 482, 484, and 490 are repeated while an object travels along the path past the array, more and more spectral intervals are resolved. When the object has passed the whole array, its spectral information can be recomposed from the stored fractions.

Upon completion of any suitable amount of information gathering in boxes 480, 482, 484, and 490, CPU 402 can perform the operation in box 492 to provide photosensed quantities, such as in the form of data for another routine or as output through external I/O 406. As shown, this operation can include combining the sensed quantities for each object so that spectral information about the object can be provided, such as in the form of a profile or other data structure.

FIG. 20 illustrates an example of how object selection routine 446 in FIG. 18 could be implemented, using spectral information provided by the operation in box 492 in FIG. 19. Routine 446 begins with the operation in box 520, which coordinates routines 440 and 442 as described above, obtaining spectral information from the operation in box 492.

The operation in box 522 receives the spectral information from box 520, such as in the form of a profile or other data structure. The operation in box 522 then compares the spectral information with other information to obtain a comparison result, such as a tentative identification of the object. The other information used in the comparison could, for example, be stored in a library of profiles or other database within memory 408, or could be embedded within routine 446. Any appropriate comparison technique could be used, including principal component analysis, in order to obtain the comparison result. The comparison could be performed directly between profiles on a pair-wise basis, or could be performed by clustering or other approaches. The result of the comparison will indicate whether the object is appropriate for further operations within analyzer 10, such as because it may be suspicious or harmful or, on the other hand, because it may be of interest for more refined analysis.

The operation in box 530 branches based on whether the object is a candidate for further operations. If not, the operation in box 532 opens a smart gate or provides appropriate control signals to perform another operation to purge the object from the active analysis channel in analyzer 10. But if the object is appropriate for further operations, the operation in box 534 ensures that the smart gate is closed or provides control signals for other suitable operations to transfer the object downstream within the active analysis channel so that a more refined analysis or a more detailed analysis can be performed, possibly after concentration of the object with other similar objects by appropriate fluidic devices.

The technique of FIG. 20 therefore illustrates an example in which an initial analysis or characterization of an object can be performed to determine whether to perform further, more refined analysis. If the initial characterization satisfies an appropriate criterion, the object can be automatically selected by operations of CPU 402 for more refined analysis. For example, the initial characterization could include scattering or fluorescence, indicating presence of a certain agent (e.g. in a smoke alarm), and the refined analysis could include multi-wavelength fluorescence, Raman scattering, or far-infrared spectroscopy; these refined techniques may in effect provide a molecular fingerprint of an agent, but usually provide only very weak signals, so that increased light-target interaction and/or increased concentration of analytes as described above are highly desirable.

In the technique in FIG. 20, an object's results from upstream sensing components generally affect operations of downstream sensing components on the same object. In a variation, it would also be possible for an object's results from particular sensing components to affect operations of parallel or upstream sensing components for other objects. More generally, the technique of FIG. 20 can be modified in various other ways to allow for exchange of information or signals indicating triggering events between sensing components.

Implementations of techniques illustrated in FIGS. 1-20 illustrate examples of apparatus that includes a fluidic structure within which a channel is defined and, along the channel, a series of sensing components that obtain information about objects traveling within respective portions of the channel. The objects are capable of emanating photons as they travel, and one of the sensing components includes a set of cells of a photosensor array. The set of cells photosense within a range of photon energies, and each of a subset of the cells photosenses in a respective subrange, with the subranges of at least two cells being different from each other.

In specific implementations of FIGS. 1-20, two of the sensing components sense within photon energy ranges that are different from each other. A sensing component can be a fluorescence spectroscope, an absorption spectroscope, a scatter spectroscope, or a Raman spectroscope. The objects can be carried within the channel by fluid, and a sensing component's portion of the channel can be an anti-resonant waveguide.

Implementations of techniques illustrated in FIGS. 1-20, and FIG. 18 in particular, also illustrate examples of a system that further includes, in addition to apparatus as described above, a processor connected to receive information about objects from sensing components in the series. In specific implementations, the processor can use information from the sensing components to obtain spectral information. The system can also include a fluidic device that receives control signals from the processor that are based on the spectral information.

Implementations of techniques illustrated in FIGS. 1-20 also illustrate examples of methods of producing an apparatus as described above.

Implementations of techniques illustrated in FIGS. 1-20 also illustrate examples of a method of obtaining information about objects. The method causes objects to travel within a channel defined within a fluidic structure while photons emanate from the objects. The method also uses a series of sensing components along the channel to obtain information about objects traveling within respective portions of the channel. One of the sensing components includes a set of cells of a photosensor array. The set of cells photosense within a range of photon energies, and each of a subset of the cells photosenses in a respective subrange, with the subranges of at least two cells being different from each other. In using the series of sensing components to obtain information, the method uses information from the one sensing component to obtain spectral information about objects traveling within its portion of the channel.

In specific implementations, such as in FIGS. 19 and 20, the method provides control signals to a fluidic device, such as a gate, based on the spectral information. The gate can be activated to direct movement of an object in the channel, such as to purge the object or to transfer it object to a downstream part of the channel. The method can further concentrate the object with other objects before they enter the downstream part of the channel. The method can use information from a first set of sensing components along an upstream part of the channel to perform initial analysis, and then use information from a second set of sensing components along the downstream part to perform a more detailed analysis.

Various of the techniques described above have been successfully implemented or simulated, including the production of a detector that includes a commercially available IC covered with a laterally graded Fabry-Perot cavity filter on a glass slide. Wavelength resolution has been experimentally determined and successfully simulated on a computer. Anti-resonant waveguide techniques have been successfully tested.

The exemplary implementations described above are advantageous because they can provide compact, inexpensive components that generally require no additional mechanical or optical parts to perform functions such as spectrometry. For example, a portable, easy-to-use spectrometer could include an analyzer as described above; a portable, compact unit could, for example, be standard equipment for emergency response teams anywhere. The results of photosensing can be read out rapidly and in parallel from a number of ICs, allowing fast data acquisition; as a result, an initial characterization of an object may be used to determine whether to perform more refined or detailed analysis of the object, or to determine which of different types of analysis are performed. A multi-signal approach like this is compatible with reagentless identification, i.e. without specific binding, tagging, labeling, dyes, or stains; also, a wide variety of objects can be identified in a wide variety of fluids, such as various nanoparticles, microorganisms, bioagents, and toxins in various aerosols, water, blood, food, and other specimens.

The implementations generally permit a continuous flow of analytes through an analyzer, allowing real-time analysis, such as in a chemical reactor for real-time feedback, and also allowing the possibility of interactive detection schemes. The use of a variety of compact optical sensing components, as described above, makes it possible to analyze objects without use of reagents, although the techniques described above could be used with reagents for excitation. Because the techniques can use a number of ICs with photosensor arrays, different ICs may address different ranges of photon energies, and a wide range may be addressed by using suitable coating materials on the ICs, possibly ranging from the ultraviolet to the far infrared and even into the terahertz range.

More generally, the implementations described above allow the combination of many different electrical and optical detection schemes on a single platform, in an approach that could be used on a wide variety of platforms. The techniques are particularly advantageous with a microfluidics architecture and an all-aerosol-based system that combines handling and unique identification of analytes on a compact, but extensible, platform.

Spectrometry measurements have a wide variety of applications, including, for example, optical instrumentation, telecommunications, fluorescence devices, process control, optical signal scanning, detection systems for chemical and biological agents, and so forth. An example of a specific application is an in-line detector for manufacturing and functionalizing colloidal particles in an industrial setting. In this application, processes typically are performed in closed systems and the properties of colloidal particles can be assessed only after all processing steps are completed. A small detection platform implemented as described above can be easily built into an on-line detector directly connected to a manufacturing vessel. As a result, small amounts of particles can be analyzed continuously in real time to determine size, chemical composition, and surface conditions. This approach permits instant process adjustments leading to production of materials with consistent properties from run to run. In-line Coulter counters for instant size measurements are already commercially available, but compact detectors as described above can also probe chemical composition using multiple advanced spectroscopic methods, an approach not previously available.

Various specific spectroscopic techniques can be implemented with the techniques described above, including absorption spectroscopy (e.g. gas sensing), fluorescence spectroscopy, and Raman spectroscopy, all of which are discussed above. The techniques described above, however, are not limited specifically to spectroscopy, but could also be applied in other photosensing situations. Additional description of applications in which photon energy is sensed in combination with relative motion is found in co-pending U.S. patent application Ser. No. 11/315,926, entitled "Sensing Photon Energies of Optical Signals", and U.S. patent application Ser. No. 11/315,386, entitled "Sensing Photon Energies Emanating From Channels or Moving Objects", both of which are incorporated herein by reference.

The exemplary implementations described above generally rely on transmission structures that include highly reflective interfaces, so that much of the incident light is reflected and only a small fraction reaches the photosensor array. Therefore, the techniques described above are especially useful in applications in which light intensity is very high or a light source emits through a large area or over an extended time. In addition, the above techniques make it possible to increase sensitivity by choosing very long integration times (without loss of throughput capacity), simpler optics, and no dispersion element. By contrast, some conventional systems such as monochromators lose all light defracted into the $0^{th}$, $2^{nd}$, and higher orders. In the implementations described above, very high light yield can be achieved by combining a transmission structure with a highly sensitive photosensor array, such as one that includes avalanche photodetectors.

In addition, components could have various shapes, dimensions, or other numerical or qualitative characteristics other than those illustrated and described above. For example, in the exemplary implementations described above, cells of a photosensor array photosense in different subranges of an application's photon energy range. The subranges of cells could have any appropriate widths and relationships, and could, for example, overlap or be distinct. The width of a cell's subrange can be chosen by designing the transmission structure and the cell sensing area; for example, the width may be as small as 0.1 nm or as great as tens of nanometers.

Some of the above exemplary implementations involve specific materials, such as in fluidic structures, photosensor arrays, and transmission structures, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, transmission structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in transmission structures may vary from 30 nm up to a few hundred nanometers.

Some of the above exemplary implementations involve particular types of transmission structures, such as Bragg mirrors and paired distributed Bragg reflectors separated by a Fabry-Perot cavity, but these transmission structures are merely exemplary, and any transmission structure that has laterally varying optical thickness could be used. Various techniques could be used to produce transmission structures with lateral variation in addition to those described above, including, during deposition, tilting the substrate, using a shadow mask, or using a temperature gradient to obtain graded layer thickness; also, during homogeneous deposition, off-axis doping, such as by e-beam, MBE, or MOVPE, could produce lateral variation.

Furthermore, various techniques other than transmission structures could be used to obtain photosensor arrays in which cells sense different subranges of photon energy.

Some of the above exemplary implementations employ an arrangement of ICs relative to fluidic structures, and a wide variety of such arrangements could be made within the scope of the invention. The invention could also be implemented with any other suitable type of photosensor array, including simple light-to-electric signal transducers arranged as cells of a photosensor array. Although objects could be photosensed one at a time, the techniques described above also allow concurrent photosensing of multiple objects. In one example, a preliminary inspection of an analyte could be made with an IC with a 400-700 nm laterally varying filter to detect fluorescence or scattering in the 400-700 nm range, after which a more refined inspection could be made with another IC, such as to perform Raman spectroscopy in the range of 100 cm$^{-1}$ to a few 1000 cm$^{-1}$. Rather than using separate ICs, different rows of a single two-dimensional photosensor array on an IC could be differently coated to photosense in different ranges.

Some of the above exemplary implementations employing fluidic structures also employ enhanced light-target interaction to obtain fluorescence. In general, however, the techniques described above could also be used for self-emitting or auto-fluorescing objects such as particles. Furthermore, various types of fluorescence, photo-luminescence, chemo-fluorescence, inelastic scattering, and so forth could be employed. The technique of anti-resonant waveguiding, described above, is only one of many techniques that could be used for enhanced light-target interaction, and any such excitation technique could be applied continuously or intermittently along a path. Various parameters could be adjusted to obtain anti-resonant waveguiding, including the shape of quartz or glass surrounding the channel; a thinner structure is generally better, with a surface parallel to the channel generally being required. Additional description of excitation techniques is found in co-pending U.S. patent application Ser. No. 11/316,660, entitled "Providing Light To Channels Or Portions" and incorporated herein by reference in its entirety.

The exemplary implementation in FIG. 18 employs a CPU, which could be a microprocessor or any other appropriate component. In general, routines as described above in relation to FIGS. 18-20 could be done either on the same IC as a photosensor array, on other components, or on a combination of the two, with any appropriate combination of software or hardware.

The above exemplary implementations generally involve production and use of photosensor arrays, ICs, transmission structures, fluidic structures, sensing components, illumination components, optical components, and analyzers following particular operations, but different operations could be performed, the order of the operations could be modified, and additional operations could be added within the scope of the invention. For example, in implementations in which a transmission structure is on a separate substrate from a photosensor array, the transmission structure could be moved relative to the photosensor array between consecutive sensing operations. Also, readout of adjusted or unadjusted sensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. Apparatus comprising:
   a fluidic structure with a channel defined therein within which objects travel, the objects being capable of emanating photons as the objects travel within the channel; and
   along the channel, a series of two or more sensing components that obtain information about objects traveling within respective portions of the channel; the series including a first sensing component that includes a respective set of cells of a photosensor array, the set of cells photosensing photons within a first range of photon energies that emanate from objects traveling within the respective portion of the channel, the set including a subset of two or more cells each of which photosenses photons in a respective subrange of the first range of photon energies, the subranges of at least two cells in the subset being different from each other.

2. The apparatus of claim 1 in which the photosensor array is included in a respective IC.

3. The apparatus of claim 2 in which the sensing components further include a second sensing component that includes a respective set of cells of a photosensor array included in a respective IC, the set of cells photosensing photons within a second range of photon energies that emanate from objects traveling within the respective portion of the channel; the first and second ranges of photon energies being different from each other.

4. The apparatus of claim 3 in which the respective set of cells of the second sensing component includes a subset of two or more cells each of which photosenses photons in a respective subrange of the second range of photon energies, the subranges of at least two cells in the subset being different from each other.

5. The apparatus of claim 4, further comprising:
   circuitry that responds to the first and second sensing components, providing signals that indicate spectral information.

6. The apparatus of claim 5 in which the circuitry further responds to all the sensing components in the series and provides signals indicating a complete spectral distribution.

7. The apparatus of claim 5 in which the signals indicate a spectral profile of an analyte, the circuitry further comparing the spectral profile with a library of spectral profiles to identify the analyte.

8. The apparatus of claim 5, further including a fluidic device connected to receive control signals from the circuitry; the circuitry providing the control signals based on the spectral information.

9. The apparatus of claim 1 in which the first sensing component is one of a fluorescence spectroscope, an absorption spectroscope, a scatter spectroscope, or a Raman spectroscope.

10. The apparatus of claim 1 in which the fluidic structure includes at least one of micromolded polydimethylsiloxane, etched glass, quartz, and patterned polymer material.

11. The apparatus of claim 1 in which the objects are carried within the channel by fluid.

12. The apparatus of claim 11 in which the first sensing component further includes:
   an excitation component that provides electromagnetic wave excitation to the objects being carried within the respective portion of the channel by the fluid, the objects emitting photons in response to the electromagnetic wave excitation.

13. The apparatus of claim 12 in which the respective portion of the channel is an anti-resonant waveguide in response to the electromagnetic wave excitation.

14. The apparatus of claim 12 in which the excitation component includes a laser or light emitting diode.

15. The apparatus of claim 12 in which the excitation component provides continuous electromagnetic wave excitation while an object is within the respective portion of the channel.

16. The apparatus of claim 11 in which the first sensing component further includes:
   an illumination component that illuminates the objects, the objects scattering photons in response to being illuminated.

17. The apparatus of claim 11, further comprising:
a fluid propelling component that propels the fluid through the channel.

18. The apparatus of claim 17 in which the fluid propelling component includes at least one of an electro-osmotic pump, a gas pressure pump, a positive displacement pump, a micro-peristaltic pump, an electro-kinetic pump, and a thermal mode pump.

19. The apparatus of claim 11 in which the first sensing component further includes:
an excitation component that adds a reagent to the fluid, the objects reacting with the reagent in the respective portion of the channel and, in response, emitting photons.

20. The apparatus of claim 11 in which the fluidic structure includes a surface that contacts the fluid, the surface including an anti-adhesion coating that allows the objects in the fluid to move without adhering to the surface.

21. The apparatus of claim 1 in which objects travel through the channel without reacting with reagents.

22. The apparatus of claim 1 in which the first sensing component further includes:
a transmission structure that transmits photons emanating from objects in the respective portion of the channel to the sensing component's set of cells, the transmission structure having a set of regions, each region transmitting photons within one of the respective subranges.

23. The apparatus of claim 22 in which the transmission structure includes a coating that varies along the channel.

24. The apparatus of claim 23 in which the coating is over the photosensor array included in the sensing component's respective IC.

25. A system that comprises the apparatus of claim 1, the system further comprising:
a processor connected to receive information about objects from at least two of the sensing components in the series.

26. The system of claim 25 in which the processor uses the information about objects to obtain spectral information about the objects.

27. The system of claim 26, further including a fluidic device connected to receive control signals from the processor; the processor providing the control signals based on the spectral information.

28. A method comprising:
producing an apparatus that includes a fluidic structure and two or more sensing components; the fluidic structure having a channel defined therein within which objects travel, the objects being capable of emanating photons as they travel within the channel; the act of producing the apparatus comprising:producing the apparatus so that the sensing components are in a series along the channel, obtaining information about objects traveling within respective portions of the channel; the series including a first sensing component that includes a respective set of cells of a photosensor array, the set of cells photosensing photons within a first range of photon energies that emanate from objects traveling within the respective portion of the channel, the set including a subset of two or more cells each of which photosenses photons in a respective subrange of the first range of photon energies, the subranges of at least two cells in the subset being different from each other.

29. A method of obtaining information about objects, the method comprising:
causing one or more objects to travel within a channel defined within a fluidic structure while photons emanate from the objects; and
using a series of sensing components along the channel, obtaining information about objects traveling within respective portions of the channel; the series including a first sensing component that includes a respective set of cells of a photosensor array, the set of cells photosensing photons within a first range of photon energies that emanate from objects traveling within the respective portion of the channel, the set including a subset of two or more cells each of which photosenses photons in a respective subrange of the first range of photon energies, the subranges of at least two cells in the subset being different from each other; the act of using the series of sensing components comprising:
using information from the first sensing component to obtain spectral information about objects traveling within its respective portion of the channel.

30. The method of claim 29, in which the act of using the series of sensing components further comprises:
using information from all the sensing components to obtain the spectral information.

31. The method of claim 29, in which the act of using the series of sensing components further comprises:
providing control signals to a fluidic device in the channel based on the spectral information.

32. The method of claim 31, in which the fluidic device is a gate that, when actuated, directs movement of one or more of the objects in the channel; the act of providing the control signals further comprising:
providing the control signals to actuate the gate.

* * * * *